United States Patent
Weaver et al.

(10) Patent No.: US 11,572,354 B2
(45) Date of Patent: Feb. 7, 2023

(54) INHIBITOR OF INDOLEAMINE 2,3-DIOXYGENASE-1 AND METHODS OF MANUFACTURE AND USE THEREOF

(71) Applicant: UNIVERSITY HEALTH NETWORK, Toronto (CA)

(72) Inventors: Donald Weaver, Toronto (CA); Michael G. Brant, Vancouver (CA); Stephanie Wohnig, Dortmund (DE); Fan Wu, Toronto (CA); Jake Goodwin-Tindall, Toronto (CA); Autumn Meek, Stillwater Lake (CA); Paolo Schiavini, Toronto (CA)

(73) Assignee: University Health Network, Toronto (CA)

( * ) Notice: Subject to any disclaimer, the term of this patent is extended or adjusted under 35 U.S.C. 154(b) by 0 days.

(21) Appl. No.: 16/961,112

(22) PCT Filed: Jan. 9, 2019

(86) PCT No.: PCT/CA2019/050031
§ 371 (c)(1),
(2) Date: Jul. 9, 2020

(87) PCT Pub. No.: WO2019/136558
PCT Pub. Date: Jul. 18, 2019

(65) Prior Publication Data
US 2021/0053942 A1    Feb. 25, 2021

Related U.S. Application Data

(60) Provisional application No. 62/615,653, filed on Jan. 10, 2018.

(51) Int. Cl.
  *C07D 403/14*  (2006.01)
  *C07D 403/04*  (2006.01)
  *C07D 401/14*  (2006.01)
(52) U.S. Cl.
  CPC ......... *C07D 403/04* (2013.01); *C07D 401/14* (2013.01)
(58) Field of Classification Search
  CPC .................................................. C07D 403/14
  See application file for complete search history.

(56) References Cited

FOREIGN PATENT DOCUMENTS

WO    2018015558 A1    1/2018

OTHER PUBLICATIONS

Brant, Michael G., "Identification of Potent Indoleamine 2, 3-Dioxygenase 1 (IDO1) Inhibitors Based on a Phenylimidazole Scaffold." ACS Medicinal Chemistry Letters 9, No. 2 (2018): 131-136.
Röhrig, Ute F., "Challenges in the Discovery of Indoleamine 2, 3-Dioxygenase 1 (IDO1) Inhibitors." Journal of Medicinal Chemistry 58, No. 24 (2015): 9421-9437.
Written Opinion of the International Searching Authority dated Mar. 26, 2019, for International Application No. PCT/CA2019/050031.
Patent Cooperation Treaty, International Search Report dated Jan. 10, 2018 for International application No. PCT/CA2019/050031.

*Primary Examiner* — Brian E McDowell
(74) *Attorney, Agent, or Firm* — Hoffmann & Baron, LLP

(57) ABSTRACT

Inhibition of indoleamine 2,3-dioxygenase (IDO1) is an attractive immunotherapeutic approach for the treatment of a variety of cancers. Dysregulation of this enzyme has also been implicated in other severe diseases such as Alzheimer's disease and arthritis. Small molecule inhibitors of Formula (Ia) and (Ib) of IDO, their synthesis, and uses thereof are provided.

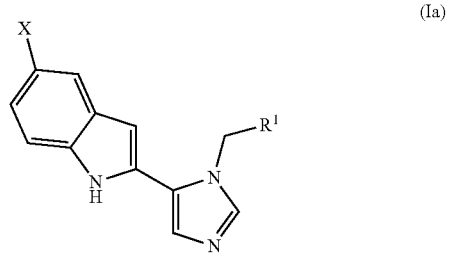

(Ia)

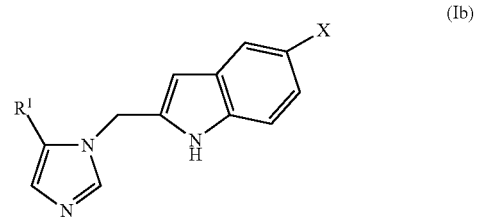

(Ib)

8 Claims, No Drawings
Specification includes a Sequence Listing.

```
                            SEQUENCE LISTING

<160> NUMBER OF SEQ ID NOS: 2

<210> SEQ ID NO 1
<211> LENGTH: 33
<212> TYPE: DNA
<213> ORGANISM: Artificial Sequence
<220> FEATURE:
<223> OTHER INFORMATION: PCR Primer

<400> SEQUENCE: 1
gtcaaccggt atggcacacg ctatggaaaa ctc                                    33

<210> SEQ ID NO 2
<211> LENGTH: 33
<212> TYPE: DNA
<213> ORGANISM: Artificial Sequence
<220> FEATURE:
<223> OTHER INFORMATION: PCR Primer

<400> SEQUENCE: 2
gtcaacgcgt ttaaccttcc ttcaaaaggg att                                    33
```

INHIBITOR OF INDOLEAMINE 2,3-DIOXYGENASE-1 AND METHODS OF MANUFACTURE AND USE THEREOF

This application is the U.S. National Phase of, and Applicant claims priority from, International Patent Application Number PCT/CA2019/050031 filed Jan. 9, 2019, which claims priority from U.S. Provisional Application Ser. No. 62/615,653 filed Jan. 10, 2018, each of which is incorporated herein by reference.

FIELD OF THE INVENTION

The present application pertains to compounds and methods for inhibition of indoleamine 2,3-dioxygenase-1. More particularly, the present application pertains to use of the compounds to treat diseases and disorders mediated by indoleamine 2,3-dioxygenase-1 and the corresponding methods of treatment.

BACKGROUND OF THE INVENTION

Over the past two decades immunotherapy has emerged as powerful tool in the treatment of many cancers. In this arena, indoleamine 2,3-dioxygenase-1 (IDO1) has received significant attention from both industry and academia. IDO1 is a heme-containing enzyme that catalyzes the oxidative cleavage of the C2-C3 indole double bond to produce N-formylkynurenine. The generated N-formylkynurenine is then further metabolized to other bioactive metabolites, including kynurenine, kynurenic acid, 3-hydroxy-kynurenine, quinolinic acid and eventually nicotinamide adenine dinucleotide (NAD). Expression of IDO1 can be induced by IFN-γ, TNF-α and other inflammatory cytokines.

Although initially identified as an important enzyme in modulating the immune response in placental tissue, IDO1 was later implicated as a key mediator of innate and adaptive immunity in the microenvironment of tumors. The expression of IDO1 by various tumor cells leads to the depletion of tryptophan in the microenvironment and subsequent block of T-cell proliferation. Dysregulation of IDO1 expression has also been implicated in the progression of several other conditions such as arthritis, inflammation, and neurological disorders such as Alzheimer's disease. Inhibition of IDO1 with a small molecule is an attractive immunotherapeutic strategy for the treatment of a wide range of cancers; discovery of additional classes of such molecules is a continued need in immuno-oncology drug design.

The above information is provided for the purpose of making known information believed by the applicant to be of possible relevance to the present invention. No admission is necessarily intended, nor should be construed, that any of the preceding information constitutes prior art against the present invention.

SUMMARY OF THE INVENTION

An object of the present application is to provide inhibitors of IDO1. The inhibitors are useful in treating disorders associated with abnormal IDO1 activity or dysregulation of IDO1 expression.

According to one aspect, the present application provides a compound, or a pharmaceutically acceptable salt thereof, of either of Formulas I is provided:

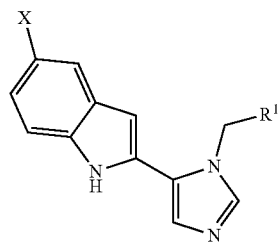

(Ia)

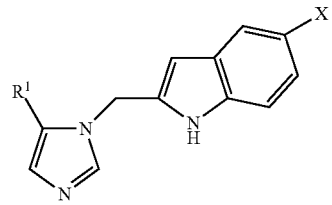

(Ib)

wherein X is H, F, Cl, or Br; $R^1$ is piperidin-2-yl, 1-phenyl-methan-1-yl-1-ol, pyrrol-2-yl, or

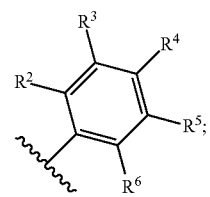

and $R^2$, $R^3$, $R^4$, $R^5$, and $R^6$ are each independently H, F, Cl, amino, hydroxy, alkoxy, cyano, trifluoromethyl, or phenyl.

In one embodiment there is provided an inhibitor compound as defined above in which $R^1$ is

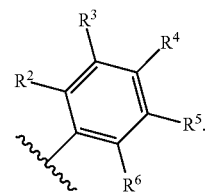

In another embodiment there is provided an inhibitor compound as defined above in which $R^4$ is H, F, Cl, amino, hydroxy, alkoxy, cyano, trifluoromethyl, or phenyl; and $R^2$, $R^3$, $R^5$, and $R^6$ are each independently H, F, Cl, amino, or hydroxy.

In another embodiment there is provided an inhibitor compound as defined above in which $R^4$ is H, F, Cl, amino, hydroxy, methoxy, or cyano.

In another embodiment there is provided an inhibitor compound as defined above in which the compound is of Formula Ia; X is Br; $R^4$ is H, methoxy, or cyano; $R^2$ is H, amino, or hydroxy; and $R^3$, $R^5$, and $R^6$ are each H.

In another embodiment there is provided an inhibitor compound as defined above in which the compound is of Formula Ib; X is F or Br; $R^6$ is H; $R^5$ is H, F, or Cl; $R^3$ and $R^4$ are each H, Cl, or hydroxy; and $R^2$ is H or hydroxy.

In another embodiment there is provided an inhibitor compound as defined above in which the compound is of Formula 1b, $R^1$ is pyrrol-2-yl, and X is F or Br.

According to another aspect, the present application provides a method of treating a disease associated with tryptophan metabolism in a subject, the method comprising administering a therapeutically effective amount to a subject of a compound, or a pharmaceutically acceptable salt thereof, of either of Formulas I:

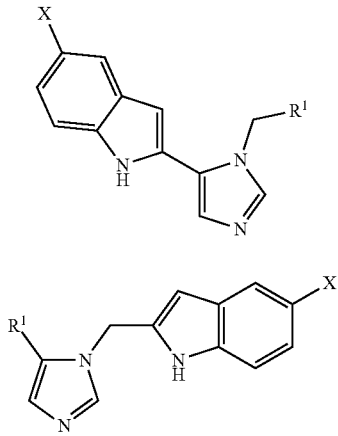

(Ia)

(Ib)

wherein
X is H, F, Cl, or Br;
$R^1$ is piperidin-2-yl, 1-phenylmethan-1-yl-1-ol, pyrrol-2-yl, or

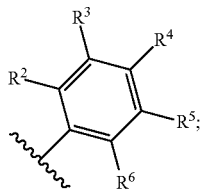

and $R^2$, $R^3$, $R^4$, $R^5$, and $R^6$ are each independently H, F, Cl, amino, hydroxy, alkoxy, cyano, trifluoromethyl, or phenyl.

In one embodiment, the method of treatment is for treating cancer, such as glioblastoma multiforme. In another embodiment, the method is for treating neurodegeneration, such as in Alzheimer's disease.

According to another aspect, the present application provides a pharmaceutical composition comprising a pharmaceutically acceptable carrier and a compound, or a pharmaceutically acceptable salt thereof, of either of Formulas I:

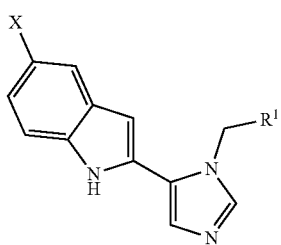

(Ia)

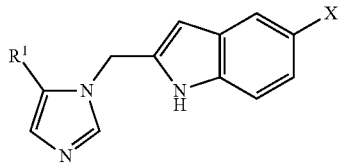

(Ib)

wherein
X is H, F, Cl, or Br;
$R^1$ is piperidin-2-yl, 1-phenyhnethan-1-yl-1-ol, pyrrol-2-yl, or

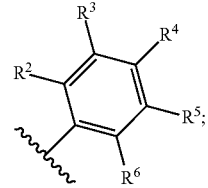

and $R^2$, $R^3$, $R^4$, $R^5$, and $R^6$ are each independently H, F, Cl, amino, hydroxy, alkoxy, cyano, trifluoromethyl, or phenyl.

According to another aspect, the present application provides a use of an inhibitor compound as defined above and in the detailed description below, for treatment of a disease or disorder associated with dysregulation of IDO1 expression or abnormal IDO1 activity in a subject in need thereof. In one embodiment, the use is for treating cancer, such as glioblastoma multiforme. In another embodiment, the method is for treating neurodegeneration, such as in Alzheimer's disease.

With the foregoing and other advantages and features of the invention that will become hereafter apparent, the nature of the invention may be more clearly understood by reference to the following detailed description of the invention and the appended claims.

DETAILED DESCRIPTION OF THE INVENTION

All patents, patent applications, and other publications referred to herein are hereby incorporated by reference in their entireties.

Definitions

Unless otherwise defined, terms as used in the specification refer to the following definitions, as detailed below.

The following abbreviations and associated terms are used herein: IDO1, indoleamine 2,3-dioxygenase 1; TDO, tryptophan 2,3-dioxygenase; 4-PI, 4-phenylimidazole; SAR, structure-activity relationship; TosMIC, tosylmethyl isocyanide; Boc₂O, di-tert-butyl dicarbonate; LDA, lithium diisopropylamide; THF, tetrahydrofuran; DMF, N,N-dimethylformamide; LE, ligand efficiency; LLE, ligand lipophilicity efficiency; Ar, aryl group.

The term "acyl" as used herein means an alkyl group, as defined herein, appended to the parent molecular moiety through a carbonyl group, as defined herein. Representative examples of acyl include, but are not limited to, acetyl, 1-oxopropyl, 2,2-dimethyl-1-oxopropyl, 1-oxobutyl, and 1-oxopentyl.

The terms "administration" or "administering" compound should be understood to mean providing a compound of the present invention to an individual in a form that can be introduced into that individual's body in an amount effective for prophylaxis, treatment, or diagnosis, as applicable. Such forms may include e.g., oral dosage forms, injectable dosage forms, transdermal dosage forms, inhalation dosage forms, and rectal dosage forms.

The term "alkoxy" as used herein means an alkyl group, as defined herein, appended to the parent molecular moiety through an oxygen atom. Representative examples of alkoxy include, but are not limited to, methoxy, ethoxy, propoxy, 2-propoxy, butoxy, tert-butoxy, pentyloxy, and hexyloxy.

The term "alkyl" as used herein means a straight or branched chain hydrocarbon containing from 1 to 20 carbon atoms, preferably from 1 to 10 carbon atoms, more preferably 1, 2, 3, 4, 5, or 6 carbons. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, and n-decyl.

The term "amido" as used herein means an amino, alkylamino, or dialkylamino group appended to the parent molecular moiety through a carbonyl group, as defined herein. Representative examples of amido include, but are not limited to, aminocarbonyl, methylaminocarbonyl, dimethylaminocarbonyl, and ethylmethylaminocarbonyl.

The term "amino" as used herein means a —$NH_2$ group.

The term "aryl" as used herein means a monocyclic hydrocarbon aromatic ring system. Representative examples of aryl include, but are not limited to, phenyl.

The term "arylalkyl" as used herein means an aryl group, as defined herein, appended to the parent molecular moiety through an alkyl group, as defined herein.

Representative examples of arylalkyl include, but are not limited to, benzyl, 2-phenylethyl and 3-phenylpropyl.

The term "carbonyl" as used herein means a —C(=O)— group.

The term "carboxy" as used herein means a —COOH group, which may be protected as an ester group: —COO-alkyl.

The term "cyano" as used herein means a —CN group.

The term "cyanophenyl" as used herein means a —CN group appended to the parent molecular moiety through a phenyl group, including, but not limited to, 4-cyanophenyl, 3-cyanophenyl, and 2-cyanophenyl.

The term "cycloalkyl" as used herein means a saturated cyclic hydrocarbon group containing from 3 to 8 carbons. Examples of cycloalkyl include cyclopropyl, cyclobutyl, cyclopentyl, cyclohexyl, cycloheptyl, and cyclooctyl.

The term "dialkylamino" as used herein means two independent alkyl groups, as defined herein, appended to the parent molecular moiety through a nitrogen atom. Representative examples of dialkylamino include, but are not limited to, dimethylamino, diethylamino, ethylmethylamino, and butylmethylamino.

The term "fluoro" as used herein means —F.

The term "fluoroalkoxy" as used herein means at least one fluoroalkyl group, as defined herein, appended to the parent molecular moiety through an oxygen group, as defined herein. Representative examples of fluoroalkyl include, but are not limited to, trifluoromethoxy ($CF_3O$—), and difluoromethoxy ($CHF_2O$—).

The term "fluoroalkyl" as used herein means at least one fluoro group, as defined herein, appended to the parent molecular moiety through an alkyl group, as defined herein.

Representative examples of fluoroalkyl include, but are not limited to, fluoromethyl, difluoromethyl, trifluoromethyl, pentafluoroethyl, and 2,2,2-trifluoroethyl.

The term "formyl" as used herein means a —C(O)H group.

The term "halo" or "halogen" as used herein means Cl, Br, I, or F.

The term "haloalkoxy" as used herein means at least one halogen, as defined herein, appended to the parent molecular moiety through an alkoxy group, as defined herein. Representative examples of haloalkoxy include, but are not limited to, 2-fluoroethoxy, trifluoromethoxy, and pentafluoroethoxy.

The term "haloalkyl" as used herein means at least one halogen, as defined herein, appended to the parent molecular moiety through an alkyl group, as defined herein. Representative examples of haloalkyl include, but are not limited to, chloromethyl, 2-fluoroethyl, trifluoromethyl, pentafluoroethyl, and 2-chloro-3-fluoropentyl.

The term "heteroaryl", as used herein, refers to an aromatic ring containing one or more heteroatoms independently selected from nitrogen, oxygen, or sulfur, or a tautomer thereof. Such rings can be monocyclic or bicyclic as further described herein. Heteroaryl rings are connected to the parent molecular moiety through a carbon or nitrogen atom.

The terms "monocyclic heteroaryl" or "5- or 6-membered heteroaryl ring", as used herein, refer to 5- or 6-membered aromatic rings containing 1, 2, 3, or 4 heteroatoms independently selected from nitrogen, oxygen, or sulfur, or a tautomer thereof. Examples of such rings include, but are not limited to, a ring wherein one carbon is replaced with an O or atom; one, two, or three N atoms arranged in a suitable manner to provide an aromatic ring; or a ring wherein two carbon atoms in the ring are replaced with one 0 or S atom and one N atom. Such rings can include, but are not limited to, a six-membered aromatic ring wherein one to four of the ring carbon atoms are replaced by nitrogen atoms, five-membered rings containing a sulfur, oxygen, or nitrogen in the ring; five membered rings containing one to four nitrogen atoms; and five membered rings containing an oxygen or sulfur and one to three nitrogen atoms. Representative examples of 5- to 6-membered heteroaryl rings include, but are not limited to, furyl, imidazolyl, isoxazolyl, isothiazolyl, oxazolyl, pyrazinyl, pyrazolyl, pyridazinyl, pyridinyl, pyrimidinyl, pyrrolyl, tetrazolyl, [1,2,3]thiadiazolyl, [1,2,3]oxadiazolyl, thiazolyl, thienyl, [1,2,3]triazinyl, [1,2,4]triazinyl, [1,3,5]triazinyl, [1,2,3]triazolyl, and [1,2,4]triazolyl.

The term "bicyclic heteroaryl" or "8- to 12-membered bicyclic heteroaryl ring", as used herein, refers to an 8-, 9-, 10-, 11-, or 12-membered bicyclic aromatic ring containing at least 3 double bonds, and wherein the atoms of the ring include one or more heteroatoms independently selected from oxygen, sulfur, and nitrogen. Representative examples of bicyclic heteroaryl rings include indolyl, benzothienyl, benzofuranyl, indazolyl, benzimidazolyl, benzothiazolyl, benzoxazolyl, benzoisothiazolyl, benzoisoxazolyl, quinolinyl, isoquinolinyl, quinazolinyl, quinoxalinyl, phthalazinyl, pteridinyl, purinyl, naphthyridinyl, cinnolinyl, thieno[2,3-d]imidazole, thieno[3,2-b]pyridinyl, and pyrrolopyrimidinyl.

The terms "heterocyclic ring" and "heterocycle", as used herein, refer to a 4- to 12-membered monocyclic or bicyclic ring containing one, two, three, four, or five heteroatoms independently selected from the group consisting of nitrogen, oxygen, and sulfur and also containing either at least one carbon atom attached to four other atoms or one carbon atom substituted with an oxo group and attached to two other atoms. Four- and five-membered rings may have zero or one double bond. Six-membered rings may have zero, one, or two double bonds. Seven- and eight-membered rings may have zero, one, two, or three double bonds. The non-aromatic heterocycle groups of the invention can be attached through a carbon atom or a nitrogen atom. The non-aromatic heterocycle groups may be present in tautomeric form. Representative examples of nitrogen-containing heterocycles include, but are not limited to, azepanyl, azetidinyl, aziridinyl, azocanyl, dihydropyridazinyl, dihydropyridinyl, dihydropyrimidinyl, morpholinyl, piperazinyl, piperidinyl, pyrrolidinyl, pyrrolinyl, dihydrothiazolyl, dihydropyridinyl, and thiomorpholinyl. Representative examples of non-nitrogen containing non-aromatic heterocycles include, but are not limited to, dioxanyl, dithianyl, tetrahydrofuryl, dihydropyranyl, tetrahydropyranyl, and [1,3]dioxolanyl.

Additional examples of heterocycles include, but are not limited to, azetidin-2-one, azepan-2-one, isoindolin-1,3-dione, (Z)-1H-benzo[e][1,4]diazepin-5(4H)-one, pyridazin-3(2H)-one, pyridin-2(1H)-one, pyrimidin-2(1H)-one, pyrimidin-2,4(1H,3H)-dione, pyrrolidin-2-one, benzo[d]thiazol-2(3H)-one, pyridin-4(1H)-one, imidazolidin-2-one, 1H-imidazol-2(3H)-one, piperidin-2-one, tetrahydropyrimidin-2(1H)-one, 1H-benzo[d]imidazol-2(3H)-one, [1,2,4]thiadiazolonyl, [1,2,5]thiadiazolonyl, [1,3,4]thiadiazinonyl, [1,2,4]oxadiazolonyl, [1,2,5]oxadiazolonyl, [1,3,4]oxadiazinonyl, and 1,5-dihydro-benzo[b][1,4]diazepin-2-on-yl.

The term "hydroxy" as used herein means an —OH group.

The term "hydroxy-protecting group" means a substituent which protects hydroxyl groups against undesirable reactions during synthetic procedures. Examples of hydroxy-protecting groups include, but are not limited to, methoxymethyl, benzyloxymethyl, 2-methoxyethoxymethyl, 2-(trimethylsilyl)ethoxymethyl, benzyl, triphenylmethyl, 2,2,2-trichloroethyl, t-butyl, trimethylsilyl, t-butyldimethylsilyl, t-butyldiphenylsilyl, methylene acetal, acetonide benzylidene acetal, cyclic ortho esters, methoxymethylene, cyclic carbonates, and cyclic boronates. Hydroxy-protecting groups are appended onto hydroxy groups by reaction of the compound that contains the hydroxy group with a base, such as triethylamine, and a reagent selected from an alkyl halide, alkyl triflate, trialkylsilyl halide, trialkylsilyl triflate, aryldialkylsilyltriflate, or an alkylchloroformate, $CH_2I_2$, or a dihaloboronate ester, for example with methyliodide, benzyl iodide, triethylsilyltriflate, acetyl chloride, benzylchloride, or dimethylcarbonate. A protecting group also may be appended onto a hydroxy group by reaction of the compound that contains the hydroxy group with acid and an alkyl acetal.

The term "nitrogen protecting group" as used herein means those groups intended to protect a nitrogen atom against undesirable reactions during synthetic procedures. Nitrogen protecting groups comprise carbamates, amides, N-benzyl derivatives, and imine derivatives. Preferred nitrogen protecting groups are acetyl, benzoyl, benzyl, benzyloxycarbonyl (Cbz), formyl, phenylsulfonyl, pivaloyl, tert-butoxycarbonyl (Boc), tert-butylacetyl, trifluoroacetyl, and triphenylmethyl (trityl). Nitrogen-protecting groups are appended onto primary or secondary amino groups by reacting the compound that contains the amine group with base, such as triethylamine, and a reagent selected from an alkyl halide, an alkyl triflate, a dialkyl anhydride, for example as represented by (alkyl-O) 2 C=O, a diaryl anhydride, for example as represented by (aryl-O) 2 C=O, an acyl halide, an alkylchloroformate, or an alkylsulfonyl-halide, an arylsulfonylhalide, or halo-CON(alkyl) 2, for example acetylchloride, benzoylchloride, benzylbromide, benzyloxycarbonylchloride, formylfluoride, phenylsulfonylchloride, pivaloylchloride, (tert-butyl-O—C=O) 2 O, trifluoroacetic anhydride, and triphenylmethylchloride.

The term "oxo" as used herein means (=O).

Unless otherwise indicated, the term "prodrug" encompasses pharmaceutically acceptable esters, carbonates, thiocarbonates, N-acyl derivatives, N-acyloxyalkyl derivatives, quaternary derivatives of tertiary amines, N-Mannich bases, Schiff bases, aminoacid conjugates, phosphate esters, metal salts and sulfonate esters of compounds disclosed herein. Examples of prodrugs include compounds that comprise a biohydrolyzable moiety (e.g., a biohydrolyzable amide, biohydrolyzable carbamate, biohydrolyzable carbonate, biohydrolyzable ester, biohydrolyzable phosphate, or biohydrolyzable ureide analog). Prodrugs of compounds disclosed herein are readily envisioned and prepared by those of ordinary skill in the art. See, e.g., Design of Prodrugs, Bundgaard, A. Ed., Elseview, 1985; Bundgaard, hours, "Design and Application of Prodrugs," A Textbook of Drug Design and Development, Krosgaard-Larsen and hours. Bundgaard, Ed., 1991, Chapter 5, p. 113-191; and Bundgaard, hours, Advanced Drug Delivery Review, 1992, 8, 1-38.

Unless otherwise indicated, the term "protecting group" or "protective group," when used to refer to part of a molecule subjected to a chemical reaction, means a chemical moiety that is not reactive under the conditions of that chemical reaction, and which may be removed to provide a moiety that is reactive under those conditions. Protecting groups are well known in the art. See, e.g., Greene, T. W. and Wuts, P. G. M., Protective Groups in Organic Synthesis (3 rd ed., John Wiley & Sons: 1999); Larock, R. C., Comprehensive Organic Transformations (2 nd ed., John Wiley & Sons: 1999). Some examples include benzyl, diphenylmethyl, trityl, Cbz, Boc, Fmoc, methoxycarbonyl, ethoxycarbonyl, and pthalimido. Protecting groups include, for example, nitrogen protecting groups and hydroxy-protecting groups.

The present application provides compounds that are useful as inhibitors of indoleamine 2,3-dioxygenase-1 (IDO1). Such compounds can be particularly useful in the treatment of diseases or disorders that are mediated by IDO1 activity. For example, the present application further provides uses and methods for the treatment of a subject affected by a disease or disorder associated with dysregulation of IDO1 expression and/or abnormal IDO1 activity.

A number of co-crystals with IDO1 have been disclosed including 4-phenylimidazole (4-PI), and members of the GDC-0919, and imidazothiazole inhibitor series. Based upon these X-ray bound co-crystals the IDO1 active site is commonly divided into three regions: pocket A, pocket B, and a heme cofactor. Aromatic, halogen-substituted aromatics or heteroaromatic motifs (such as indole) are most frequently chosen to occupy pocket A. Pocket B contains a mixture of hydrophilic (Arg-231) and hydrophobic (Phe) residues. The heme cofactor contains two distinct structural features: the porphyrin-bound iron atom, and a propionate residue which projects into the binding site.

Provided herein are inhibitors of IDO1 that have been designed based on modelling studies such that they are anticipated to bind in all three regions of the IDO1 active site. These inhibitors have now been found to selectively inhibit IDO1.

In one aspect, the present application provides an inhibitor compound, or a pharmaceutically acceptable salt thereof, that comprises an optionally-substituted indolyl group bound directly, or via a methylene group, to an optionally-substituted imidazole group. According to one embodiment, the inhibitor is a compound of Formula Ia or Ib:

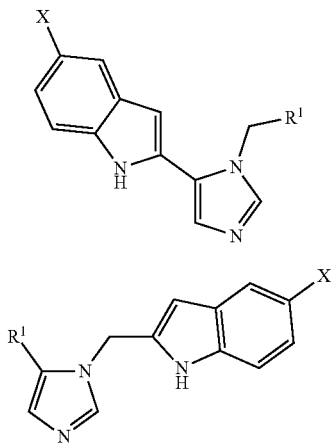

wherein
X is H, F, Cl, or Br;
R¹ is piperidin-2-yl, 1-phenylmethan-1-yl-1-ol, pyrrol-2-yl, or

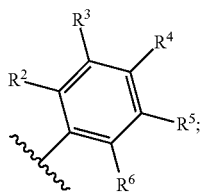

and R², R³, R⁴, R⁵, and R⁶ are each independently H, F, Cl, amino, hydroxy, alkoxy, cyano, trifluoromethyl, or aryl, such as, phenyl.

In one embodiment there is provided an IDO1 inhibitor compound of Formula Ia or Ib in which R¹ is

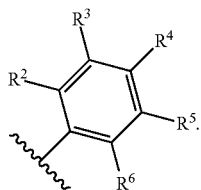

In an example of this embodiment, R⁴ is H, F, Cl, amino, hydroxy, alkoxy, cyano, trifluoromethyl, or phenyl; and R², R³, R⁵, and R⁶ are each independently H, F, Cl, amino, or hydroxyl. In another example, R⁴ is H, F, Cl, amino, hydroxy, methoxy or cyano.

In accordance with another embodiment, there is provided an IDO1 inhibitor that is a compound of Formula Ia in which X is Br; R⁴ is H, methoxy, or cyano, R² is H, amino or hydroxyl; and R³, R⁵, and R⁶ are each H.

In accordance with another embodiment, there is provided an IDO1 inhibitor that is a compound of Formula Ib in which X is Br or F; R⁶ is H; R⁵ is H, F, or Cl; R³ and R⁴ are each H, Cl, or hydroxy; and R² is H or hydroxy.

In accordance with a further embodiment, there is provided an IDO1 inhibitor that is a compound of Formula Ib in which R¹ is pyrrol-2-yl, and X is F or Br.

The compounds of the invention can be used in the form of pharmaceutically acceptable salts derived from inorganic or organic acids. Pharmaceutically acceptable salt(s) are well-known in the art. For clarity, the term "pharmaceutically acceptable salts" as used herein generally refers to salts prepared from pharmaceutically acceptable non-toxic acids or bases including inorganic acids and bases and organic acids and bases. Suitable pharmaceutically acceptable base addition salts include metallic salts made from aluminum, calcium, lithium, magnesium, potassium, sodium and zinc or organic salts made from lysine, N,N'-dibenzylethylenediamine, chloroprocaine, choline, diethanolamine, ethylenediamine, meglumine (N-methylglucamine) and procaine. Suitable non-toxic acids include inorganic and organic acids such as acetic, alginic, anthranilic, benzenesulfonic, benzoic, camphorsulfonic, citric, ethenesulfonic, formic, fumaric, furoic, galacturonic, gluconic, glucuronic, glutamic, glycolic, hydrobromic, hydrochloric, isethionic, lactic, maleic, malic, mandelic, methanesulfonic, mucic, nitric, pamoic, pantothenic, phenylacetic, phosphoric, propionic, salicylic, stearic, succinic, sulfanilic, sulfuric, tartaric acid, and p-toluenesulfonic acid. Specific non-toxic acids include hydrochloric, hydrobromic, phosphoric, sulfuric, and methanesulfonic acids. Examples of specific salts thus include hydrochloride and mesylate salts. Others are well-known in the art. See, e.g., Remington's Pharmaceutical Sciences, 18 th ed. (Mack Publishing, Easton Pa.: 1990) and Remington: The Science and Practice of Pharmacy, 19 th ed. (Mack Publishing, Easton Pa.: 1995). The preparation and use of acid addition salts, carboxylate salts, amino acid addition salts, and zwitterion salts of compounds of the present invention may also be considered pharmaceutically acceptable if they are, within the scope of sound medical judgment, suitable for use in contact with the tissues of humans and lower animals without undue toxicity, irritation, allergic response, and the like, are commensurate with a reasonable benefit/risk ratio, and are effective for their intended use. Such salts may also include various solvates and hydrates of the compound of the present invention.

The compounds of the invention can be used in the form of pharmaceutically acceptable solvates. Pharmaceutically acceptable solvate(s) are well-known in the art. For clarity, the term "pharmaceutically acceptable solvates" as used herein generally refers to solvates prepared from pharmaceutically acceptable non-toxic solvents. A pharmaceutically acceptable solvate is an aggregate that consists of an inhibitor compound with one or more pharmaceutically acceptable, non-toxic solvent molecules. A hydrate is one example of a pharmaceutically acceptable solvate. In another example, the solvent in the solvate can be an alcohol, examples of which are 1-butanol, 2-butanol, ethanol, 2-ethoxyethanol, ethylene glycol, isopropanol, 2-methoxyethanol, 3-methyl-1-butanol, 1-pentanol and 1-propanol.

Certain compounds of the present invention may be isotopically labelled, e.g., with various isotopes of carbon, fluorine, or iodine, as applicable when the compound in question contains at least one such atom.

Certain compounds of the present invention may exist as stereoisomers wherein, asymmetric or chiral centers are present. These stereoisomers are "R" or "S" depending on the configuration of substituents around the chiral carbon atom. The terms "R" and "S" used herein are configurations as defined in IUPAC 1974 Recommendations for Section E, Fundamental Stereochemistry, in Pure Appl. Chem., 1976, 45: 13-30. The invention contemplates various stereoisomers and mixtures thereof and these are specifically included within the scope of this invention. Stereoisomers include enantiomers and diastereomers, and mixtures of enantiomers or diastereomers. Individual stereoisomers of compounds of the invention may be prepared synthetically from commercially available starting materials which contain asymmetric or chiral centers or by preparation of racemic mixtures followed by resolution well known to those of ordinary skill in the art. These methods of resolution are exemplified by (1) attachment of a mixture of enantiomers to a chiral auxiliary, separation of the resulting mixture of diastereomers by recrystallization or chromatography and optional liberation of the optically pure product from the auxiliary as described in Furniss, Hannaford, Smith, and Tatchell, "Vogel's Textbook of Practical Organic Chemistry", 5th edition (1989), Longman Scientific & Technical, Essex CM20 2JE, England, or (2) direct separation of the mixture of optical enantiomers on chiral chromatographic columns or (3) fractional recrystallization methods.

Certain compounds of the present invention may exist as cis or trans isomers, wherein substituents on a ring may attached in such a manner that they are on the same side of the ring (cis) relative to each other, or on opposite sides of the ring relative to each other (trans). Such methods are well known to those of ordinary skill in the art, and may include separation of isomers by recrystallization or chromatography. It should be understood that the compounds of the invention may possess tautomeric forms, as well as geometric isomers, and that these also constitute an aspect of the invention.

It should be noted that a chemical moiety that forms part of a larger compound may be described herein using a name commonly accorded it when it exists as a single molecule or a name commonly accorded its radical. For example, the terms "pyridine" and "pyridyl" are accorded the same meaning when used to describe a moiety attached to other chemical moieties. Thus, for example, the two phrases "XOH, wherein X is pyridyl" and "XOH, wherein X is pyridine" are accorded the same meaning, and encompass the compounds pyridin-2-ol, pyridin-3-ol and pyridin-4-ol.

It should also be noted that names of compounds having one or more chiral centers that do not specify the stereochemistry of those centers encompass pure stereoisomers and mixtures thereof. Moreover, any atom shown in a drawing with unsatisfied valences is assumed to be attached to enough hydrogen atoms to satisfy the valences. In addition, chemical bonds depicted with one solid line parallel to one dashed line encompass both single and double (e.g., aromatic) bonds, if valences permit.

According to some embodiments, there is provided an IDO1 inhibitor compound, as described above, which is substantially pure. The term "substantially pure" means that the isolated material is at least 90% pure, preferably 95% pure, even more preferably 99% pure as assayed by analytical techniques known in the art.

Pharmaceutical Compositions

The present application further provides compositions comprising one or more IDO1 inhibitor as described herein, or a pharmaceutically acceptable salt or solvate thereof. Such compositions can be used in the treatment of diseases or disorders characterized by or associated with a dysregulation of IDO1 expression or abnormal IDO1 activity. These pharmaceutical compositions comprise one or more IDO1 inhibitor as described herein, or a pharmaceutically acceptable salt or solvate thereof, and one or more pharmaceutically acceptable excipient.

The term "pharmaceutically acceptable excipient", as used herein, means a non-toxic, inert solid, semi-solid or liquid filler, diluent, encapsulating material or formulation auxiliary of any type. Some examples of materials which can serve as pharmaceutically acceptable carriers are sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; cocoa butter and suppository waxes; oils such as peanut oil, cottonseed oil, safflower oil, sesame oil, olive oil, corn oil and soybean oil; glycols; such a propylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of one skilled in the art of formulations.

The pharmaceutical compositions can be formulated for oral administration in solid or liquid form, for parenteral intravenous, subcutaneous, intramuscular, intraperitoneal, intra-arterial, or intradermal injection, for or for vaginal, nasal, topical, or rectal administration. Pharmaceutical compositions of the present invention suitable for oral administration can be presented as discrete dosage forms, e.g., tablets, chewable tablets, caplets, capsules, liquids, and flavored syrups. Such dosage forms contain predetermined amounts of active ingredients, and may be prepared by methods of pharmacy well known to those skilled in the art. See generally, Remington's Pharmaceutical Sciences, 18th ed., Mack Publishing, Easton Pa. (1990).

Parenteral dosage forms can be administered to patients by various routes including subcutaneous, intravenous (including bolus injection), intramuscular, and intraarterial. Because their administration typically bypasses patients' natural defenses against contaminants, parenteral dosage forms are specifically sterile or capable of being sterilized prior to administration to a patient. Examples of parenteral dosage forms include solutions ready for injection, dry products ready to be dissolved or suspended in a pharmaceutically acceptable vehicle for injection, suspensions ready for injection, and emulsions. Pharmaceutical compositions for parenteral injection comprise pharmaceutically acceptable sterile aqueous or nonaqueous solutions, dispersions, suspensions or emulsions and sterile powders for reconstitution into sterile injectable solutions or dispersions. Examples of suitable aqueous and nonaqueous carriers, diluents, solvents or vehicles include water, ethanol, polyols (propylene glycol, polyethylene glycol, glycerol, and the like, and suitable mixtures thereof), vegetable oils (such as olive oil) and injectable organic esters such as ethyl oleate, or suitable mixtures thereof. Suitable fluidity of the composition may be maintained, for example, by the use of a coating such as lecithin, by the maintenance of the required particle size in the case of dispersions, and by the use of surfactants. These compositions may also contain adjuvants such as preservative agents, wetting agents, emulsifying agents, and dispersing agents. Prevention of the action of microorganisms may be ensured by various antibacterial and antifungal agents, for example, parabens, chlorobutanol, phenol, sorbic acid, and the like. It may also be desirable to include isotonic agents, for example, sugars, sodium chloride and the like. Prolonged absorption of the injectable pharmaceutical form may be brought about by the use of agents delaying absorption, for example, aluminum monostearate and gelatin.

In some cases, in order to prolong the effect of a drug, it is often desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Suspensions, in addition to the active compounds, may contain suspending agents, for example, ethoxylated isostearyl alcohols, polyoxyethylene sorbitol and sorbitan esters, microcrystalline cellulose, aluminum metahydroxide, bentonite, agar-agar, tragacanth, and mixtures thereof. If desired, and for more effective distribution, the compounds of the invention can be incorporated into slow-release or targeted-delivery systems such as polymer matrices, liposomes, and microspheres. They may be sterilized, for example, by filtration through a bacteria-retaining filter or by incorporation of sterilizing agents in the form of sterile solid compositions, which may be dissolved in sterile water or some other sterile injectable medium immediately before use.

Injectable depot forms are made by forming microencapsulated matrices of the drug in biodegradable polymers such as polylactide-polyglycolide. Depending upon the ratio of drug to polymer and the nature of the particular polymer employed, the rate of drug release can be controlled. Examples of other biodegradable polymers include poly (orthoesters) and poly(anhydrides). Depot injectable formulations also are prepared by entrapping the drug in liposomes or microemulsions which are compatible with body tissues. The injectable formulations can be sterilized, for example, by filtration through a bacterial-retaining filter or by incorporating sterilizing agents in the form of sterile solid compositions which can be dissolved or dispersed in sterile water or other sterile injectable medium just prior to use.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic, parenterally acceptable diluent or solvent such as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

Solid dosage forms for oral administration include capsules, tablets, pills, powders, and granules. In such solid dosage forms, one or more compounds of the invention is mixed with at least one inert pharmaceutically acceptable carrier such as sodium citrate or dicalcium phosphate and/or a) fillers or extenders such as starches, lactose, sucrose, glucose, mannitol, and salicylic acid; b) binders such as carboxymethylcellulose, alginates, gelatin, polyvinylpyrrolidinone, sucrose, and acacia; c) humectants such as glycerol; d) disintegrating agents such as agar-agar, calcium carbonate, potato or tapioca starch, alginic acid, certain silicates, and sodium carbonate; e) solution retarding agents such as paraffin; f) absorption accelerators such as quaternary ammonium compounds; g) wetting agents such as cetyl alcohol and glycerol monostearate; h) absorbents such as kaolin and bentonite clay; and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using lactose or milk sugar as well as high molecular weight polyethylene glycols. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract in a delayed manner. Examples of materials which can be useful for delaying release of the active agent can include polymeric substances and waxes.

Liquid dosage forms for oral administration include pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, and perfuming agents. Dosage forms for topical or transdermal administration of a compound of this invention include ointments, pastes, creams, lotions, gels, powders, solutions, sprays, inhalants or patches. A desired compound of the invention is admixed under sterile conditions with a pharmaceutically acceptable carrier and any needed preservatives or buffers as may be required. Ophthalmic formulation, ear drops, eye ointments, powders and solutions are also contemplated as being within the scope of this invention. The ointments, pastes, creams and gels may contain, in addition to an active compound of this invention, animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to the compounds of this invention, lactose, talc, silicic acid, aluminum hydroxide, calcium silicates and polyamide powder, or mixtures of these substances. Sprays can additionally contain customary propellants such as chlorofluorohydrocarbons.

Compounds of the invention may also be administered in the form of liposomes. As is known in the art, liposomes are generally derived from phospholipids or other lipid substances. Liposomes are formed by mono- or multi-lamellar hydrated liquid crystals that are dispersed in an aqueous medium. Any non-toxic, physiologically acceptable and metabolizable lipid capable of forming liposomes may be used. The present compositions in liposome form may contain, in addition to the compounds of the invention, stabilizers, preservatives, and the like. The preferred lipids are the natural and synthetic phospholipids and phosphatidylcholines (lecithins) used separately or together. Methods to form liposomes are known in the art. See, for example, Prescott, Ed., Methods in Cell Biology, Volume XIV, Academic Press, New York, N.Y., (1976), p 33 et seq.

Actual dosage levels of active ingredients in the pharmaceutical compositions of this invention can be varied so as to obtain an amount of the active compound(s) that is effective to achieve the desired therapeutic response for a particular patient, compositions and mode of administration. The selected dosage level will depend upon the activity of the particular compound, the route of administration, the severity of the condition being treated and the condition and prior medical history of the patient being treated. However, it is within the skill of the art to start doses of the compound at levels lower than required to achieve the desired therapeutic effect and to gradually increase the dosage until the desired effect is achieved.

An effective amount of one of the compounds of the invention can be employed in pure form or, where such forms exist, in a pharmaceutically acceptable salt form or a pharmaceutically acceptable solvate form. Alternatively or in addition, the compound can be administered as a pharmaceutical composition containing the compound of interest in combination with one or more pharmaceutically acceptable carriers. It will be understood, however, that the total daily usage of the compounds and compositions of the invention will be decided by the attending physician within the scope of sound medical judgment. The specific effective dose level for any particular patient will depend upon a variety of factors including the disorder being treated and the severity of the disorder; activity of the specific compound employed; the specific composition employed; the age, body weight, general health, sex and diet of the patient; the time of administration, route of administration, and rate of excretion of the specific compound employed; the duration of the treatment; the risk/benefit ratio; drugs used in combination or coincidental with the specific compound employed; and like factors well known in the medical arts. For example, it is well within the skill of the art to start doses of the compound at levels lower than required to achieve the desired therapeutic effect and to gradually increase the dosage until the desired effect is achieved.

The total daily dose of the compounds of the present invention as administered to a human or lower animal may range from about 0.0003 to about 30 mg/kg of body weight. For purposes of oral administration, more preferable doses can be in the range of from about 0.0003 to about 1 mg/kg body weight. If desired, the effective daily dose can be divided into multiple doses for purposes of administration; consequently, single dose compositions may contain such amounts or submultiples thereof to make up the daily dose. For oral administration, the compositions of the invention are preferably provided in the form of tablets containing about 1.0, about 5.0, about 10.0, about 15.0, about 25.0, about 50.0, about 100, about 250, or about 500 milligrams of the active ingredient.

Methods of Treatment

In another aspect, the present application provides a method of treating a disease or disorder associated with dysregulation of IDO1 expression and/or abnormal IDO1 activity. In another aspect, there is provided a method for preventing onset or progression of a disease or disorder associated with dysregulation of IDO1 expression and/or abnormal IDO1 activity. Typically, such diseases or disorders are characterized by or associated with increased IDO1 expression or activity.

These methods comprises administering a therapeutically effective amount to a subject of a compound, or a pharmaceutically acceptable salt or solvate thereof, of Formula Ia or Ib:

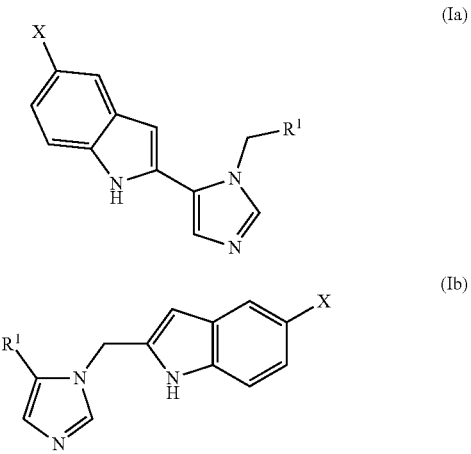

wherein

X is H, F, Cl, or Br;

$R^1$ is piperidin-2-yl, 1-phenylmethan-1-yl-1-01, pyrrol-2-yl, or

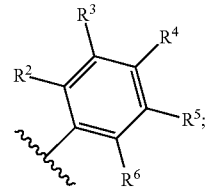

and $R^2$, $R^3$, $R^4$, $R^5$, and $R^6$ are each independently H, F, Cl, amino, hydroxy, alkoxy, cyano, trifluoromethyl, or phenyl.

In one embodiment, the method is for treating a disease associated with tryptophan metabolism. For example, the disease can be cancer, such as glioblastoma multiforme, neurodegeneration or Alzheimer's disease.

In a related aspect, the present application provides a use of a compound, or a pharmaceutically acceptable salt or solvate thereof, of Formula Ia or Ib:

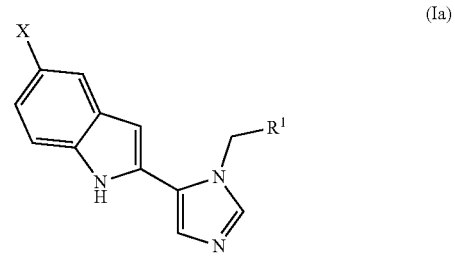

-continued

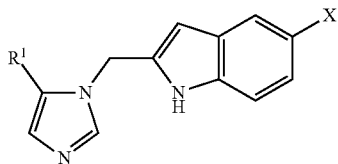

(Ib)

wherein
X is H, F, Cl, or Br;
R¹ is piperidin-2-yl, 1-phenylmethan-1-yl-1-ol, pyrrol-2-yl, or

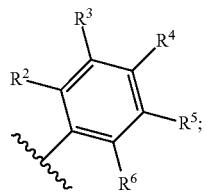

and R², R³, R⁴, R⁵, and are each independently H, F, Cl, amino, hydroxy, alkoxy, cyano, trifluoromethyl, or phenyl, for: (i) treatment of a disease or disorder associated with dysregulation of IDO1 expression or abnormal IDO1 activity in a subject in need thereof; or (ii) for prevention of onset or progression of the disease or disorder associated with dysregulation of IDO1 expression or abnormal IDO1 activity in a subject in need thereof.

In one embodiment, the inhibitor compounds of the present application can be used in combination with one or more additional therapeutic agent that are being used and/or developed to treat cancers or other diseases or disorders that are associated with dysregulation of IDO1 expression or abnormal IDO1 activity, e.g., inflammatory disorders, Alzheimers' disease. The one or more additional therapeutic agent may be, for example, a chemotherapeutic agent, an immunotherapeutic agent, a radiotherapeutic agent, an antineoplastic agent, an anti-cancer agent, an anti-proliferation agent, an anti-fibrotic agent, an anti-angiogenic agent, a therapeutic antibody, or any combination thereof.

Unless otherwise indicated, the terms "prevent," "preventing" and "prevention" contemplate an action that occurs before a patient begins to suffer from the specified disease or disorder, which inhibits or reduces the severity of the disease or disorder or of one or more of its symptoms. The terms encompass prophylaxis.

Unless otherwise indicated, a "prophylactically effective amount" of a compound is an amount sufficient to prevent a disease or condition, or one or more symptoms associated with the disease or condition, or prevent its recurrence. A prophylactically effective amount of a compound is an amount of therapeutic agent, alone or in combination with other agents, which provides a prophylactic benefit in the prevention of the disease. The term "prophylactically effective amount" can encompass an amount that improves overall prophylaxis or enhances the prophylactic efficacy of another prophylactic agent.

Unless otherwise indicated, a "diagnostically effective amount" of a compound is an amount sufficient to diagnose a disease or condition. In general, administration of a compound for diagnostic purposes does not continue for as long as a therapeutic use of a compound, and might be administered only once if such is sufficient to produce the diagnosis.

Unless otherwise indicated, a "therapeutically effective amount" of a compound is an amount sufficient to treat a disease or condition, or one or more symptoms associated with the disease or condition.

The term "subject" is intended to include living organisms in which disease may occur. Examples of subjects include humans, monkeys, cows, sheep, goats, dogs, cats, mice, rats, and transgenic species thereof.

EXAMPLES

Example 1—Characterization Methods $^1$H/$^{13}$C NMR spectra were recorded on a Bruker Ultrashield™ (300/75 MHz) and Agilent (700/175 MHz) spectrometers at ambient probe temperatures using residual undeuterated solvent as an internal reference.[1] Data are presented as follows: chemical shift (in ppm on a δ scale relative to $δ_{TMS}$=0), multiplicity (s=singlet, d=doublet, t=triplet, q=quartet, qn=quintet, sep=septet, m=multiplet, br=broad), coupling constant (J/Hz) and integration.

Mass spectra were recorded using electron spray ionisation (ESI⁺) with a Xevo TQ-XS Tandem Triple Quadrupole Mass Spectrometer. The parent ion [M+H]⁺ is quoted. Purity was determined using either a Waters Aquity UPLC® (2.1× 50 mm, 1.7 μm particle size) or a Waters 1525EF Binary HPLC pump/Silia Chrom® SB C18 (4.6×250 nm, 5.0 μm particle size) with a Waters 2487 Dual λ Absorbance Detector. For both instruments elution with a water/0.1% formic acid and acetonitrile gradient was used with a flow rate of 0.60 mL/min (5 and 15 minute run times respectively). UV detection was carried out at a wavelength of 254 nm.

Analytical thin layer chromatography (TLC) was carried out on Merck Kieselgel 60 $F_{254}$ plates with visualisation by ultraviolet light (254 nm) and potassium permanganate or phosphomolybdic acid/$Ce_2(SO_4)_3$ dips. Flash chromatography was carried out on RediSep columns using an Isco CombiFlash SG100c.

Reagents and solvents were purified by standard means (e.g., by following relevant directions in D. D. Perrin, W. L. F. A., Purification of Laboratory Chemicals. 1988). All experiments were performed under anhydrous conditions under an atmosphere of argon, except where stated, using oven-dried apparatus and employing standard techniques for handling air-sensitive materials. Unless stated otherwise, reactions were performed at room temperature (RT). Describe various experimental setups by subtitle, then start numbering with IUPAC names as subtitles. The starting materials are either commercially available or may be prepared from commercially available reagents using chemical reactions known in the art.

Example 2—"Series 1" Inhibitors

In this Example, a series of inhibitor compounds as described above were synthesized. The inhibitor compounds were designed to include a suitable lipophilic group, such as a 5-bromoindole ring, for occupying pocket A of the IDO1 active site. Further, without wishing to be bound by theory, incorporation of an imidazole group attached to the C2 position of the indole could bind Fe²⁺ and the free NH of the imidazole could hydrogen bond to Ser167 of the IDO1 active site. This design was supported by computational modelling (using PDB ID: 2DOT as a template) which indicated that an imidazole attached to the C2 position of 5-bromoindole would be orientated at an appropriate vector to bind $Fe^{2+}$. These "Series 1" compounds are generally denoted herein by a compound number starting with "9".

The general synthetic pathway employed to generate the Series 1 inhibitors is shown below:

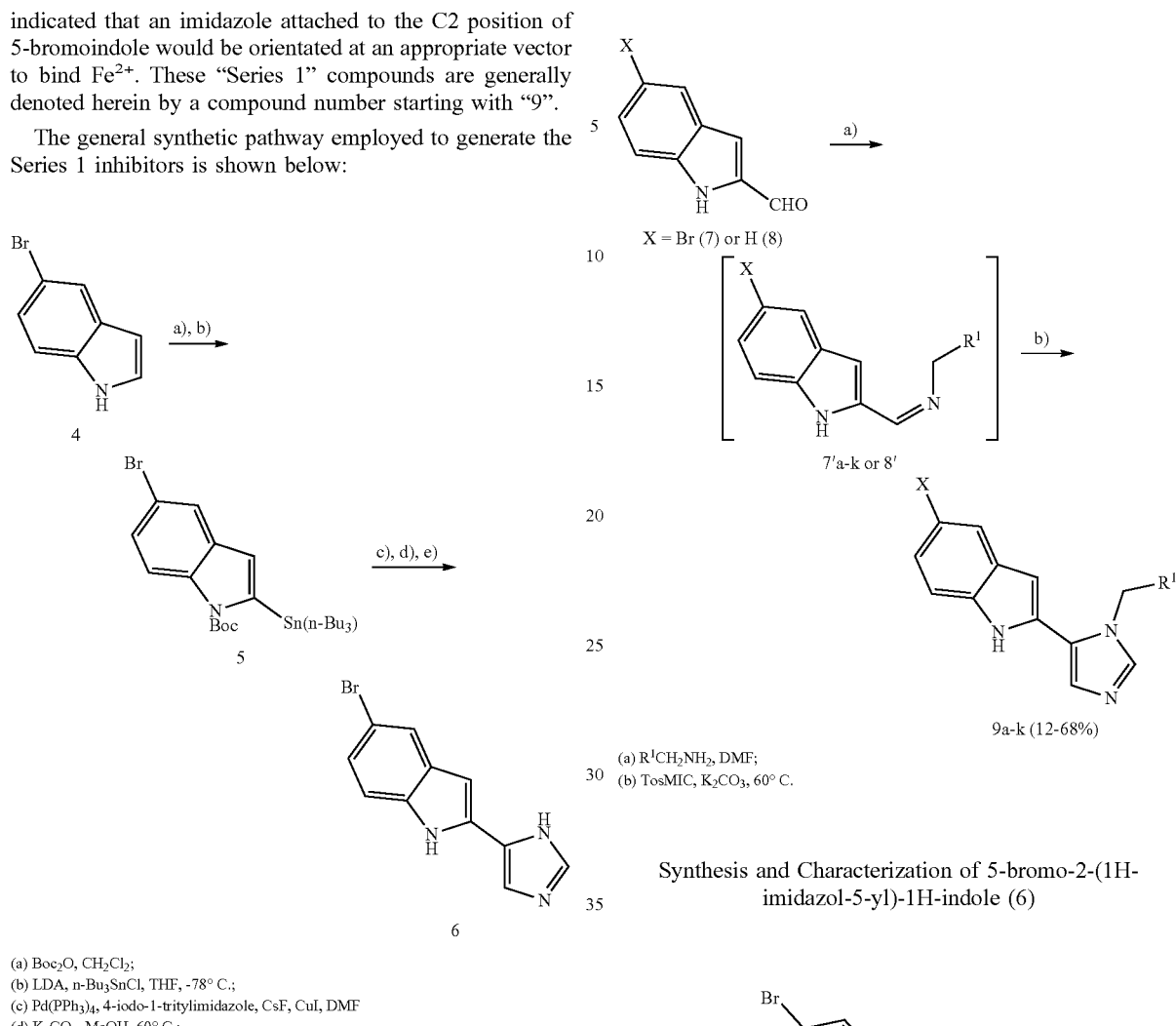

(a) $Boc_2O$, $CH_2Cl_2$;
(b) LDA, n-$Bu_3SnCl$, THF, -78° C.;
(c) $Pd(PPh_3)_4$, 4-iodo-1-tritylimidazole, CsF, CuI, DMF
(d) $K_2CO_3$, MeOH, 60° C.;
(e) AcOH, MeOH, 80° C.

5-bromo-2-imidazoindole (6) was synthesized in a 5-step sequence. Commercially available 5-bromoindole (4) was protected with a Boc group and then stannylated at the C2 position to provide compound 5. A Stille coupling was then utilized to attach a trityl protected imidazole ring. This was followed by protecting group removal to furnish the target molecule. The inhibitory activity of 6 was determined against IDO using an in vitro assay described in the Examples below and was measured to be 30 µM. Despite the modest gain in potency of 6 versus 4-PI, compound 6 was evaluated as a suitably versatile scaffold for the generation of analogs.

To progress compound 6 the strategy focused on increasing potency through addition of suitable side-chains to occupy pocket B. Molecular modelling studies indicated an aromatic group bridged by an appropriate spacer (i.e. methylene) attached to the N3-position of the imidazole would extend into pocket B. To demonstrate this, compounds 9a-k were synthesized in two steps (one pot) using the van Leusen imidazole synthesis protocol. As such, imine formation between the appropriate benzyl amine and 2-indolecarboxaldeyde (7 or 8), followed by subsequent reaction with TosMIC provided indole-imidazoles 9a-k.

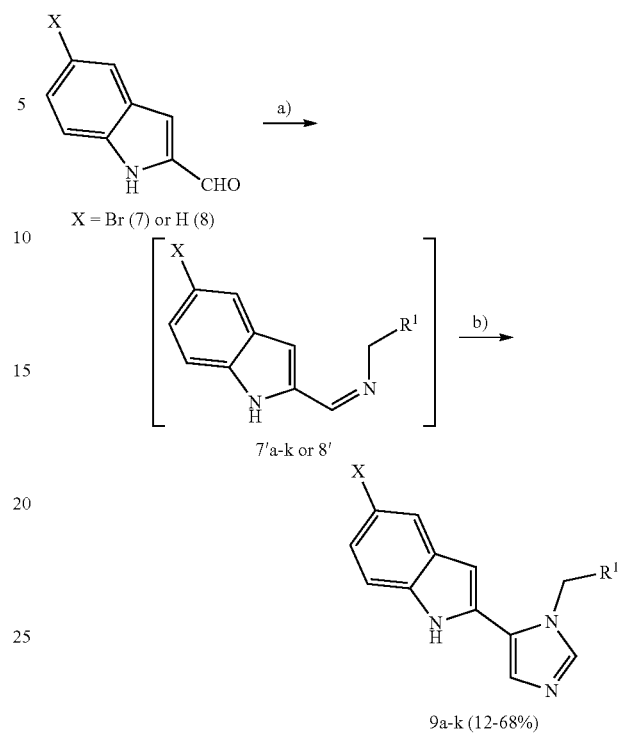

(a) $R^1CH_2NH_2$, DMF;
(b) TosMIC, $K_2CO_3$, 60° C.

Synthesis and Characterization of 5-bromo-2-(1H-imidazol-5-yl)-1H-indole (6)

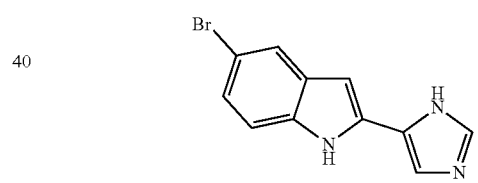

To a stirred solution of 5-bromoindole 6 (3.92 g, 20.0 mmol) in $CH_2Cl_2$ (50 mL) was added DMAP (0.24 g, 2.00 mmol) and di-tert-butyl dicarbonate (4.80 g, 22.0 mmol). The reaction mixture was stirred overnight before being diluted with EtOAc (20 mL), washed with HCl (0.1 N aqueous) and brine. The organic extract was dried ($Na_2SO_4$) and concentrated in vacuo to afford tert-butyl 5-bromo-1H-indole-1-carboxylate as a clear oil. The crude product was used directly in the next step without further purification.

To a stirred solution of tert-butyl 5-bromo-1H-indole-1-carboxylate (1.48 g, 5.00 mmol) in THF (15 mL) was added dropwise LDA (6.0 mL, 1.0 M in THF, 6.00 mmol) at -78° C. The reaction mixture was stirred for 1 h at -78° C. before n-$Bu_3SnCl$ (1.65 mL, 6.08 mmol) was added. After stirring for 1 h at -78° C. the reaction mixture was quenched with saturated aqueous ammonium chloride (10 mL). The layers were separated and the aqueous phase was extracted with EtOAc (2×25 mL). The combined organic extracts were washed with brine, dried ($Na_2SO_4$) and concentrated in vacuo to afford tert-butyl 5-bromo-2-(tributylstannyl)-1H-indole-1-carboxylate as a clear oil.

The crude residue (2.18 g, 5.00 mmol) was dissolved in DMF (20 mL) and tetrakis(triphenylphosphine)palladium(0) (0.29 g, 0.25 mmol), CuI (95.0 mg, 0.50 mmol) followed by CsF (1.52 g, 10.00 mmol) were added. The solution was degassed for 10 minutes and the reaction mixture was heated to 50° C. and stirred overnight. The reaction mixture was quenched with H$_2$O (10 mL), the layers were separated and the aqueous phase was extracted with EtOAc (2×25 mL). The combined organic extracts were washed with brine, dried (Na$_2$SO$_4$) and concentrated in vacuo to afford tert-butyl 5-bromo-2-(1-trityl-1H-imidazol-4-yl)-1H-indole-1-carboxylate. The crude residue was dissolved in THF/MeOH/H$_2$O (5:6:3, 70 mL). K$_2$CO$_3$ (1.60 g, 11.59 mmol) was added and the reaction mixture was heated to 70° C. and stirred overnight before being cooled to RT and concentrated in vacuo. The residue was suspended in H$_2$O (20 mL) and EtOAc (20 mL). The layers were separated and the aqueous phase was extracted with EtOAc (2×20 mL). The combined organic extracts were washed with brine, dried (Na$_2$SO$_4$) and concentrated in vacuo. The crude residue was then dissolved in MeOH/AcOH (2:1, 30 mL), heated to 70° C. and stirred overnight. The reaction mixture was then cooled to RT and concentrated in vacuo. Purification by column chromatography (MeOH/CH$_2$Cl$_2$, 0:100→5:95 gradient run) afforded 5-bromo-2-(1H-imidazol-5-yl)-1H-indole 6 as an off-white solid.

$^1$H NMR (DMSO-d6, 300 MHz) δ 12.32 (br s, 1H), 11.48 (br s, 1H), 7.77 (s, 1H), 7.63 (s, 1H), 7.58 (s, 1H), 7.39 (d, J=8.57 Hz, 1H), 7.11 (dd, J=1.49 Hz, J=8.57 Hz, 1H), 6.59 (s, 1H); $^{13}$C NMR (acetone-d6, 75 MHz) 137.4, 137.0, 136.8, 135.3, 133.0, 124.8, 123.4, 115.6, 114.3, 113.6, 97.5; HRMS (ESI) calculated for C$_{11}$H$_8$BrN$_3$ [M+H]$^+$: 261.9980. Found: 261.9985. Purity by UPLC: 99% (t$_R$=1.23 min).

Synthesis of 2-(1-benzyl-1H-imidazol-5-yl)-1H-indole (9b)

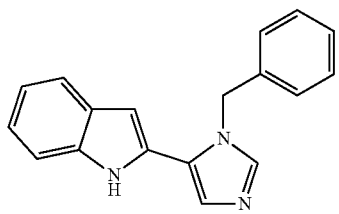 [SMILES: c1ccc(Cn2cncc2-c2cc3ccccc3[nH]2)cc1]

To a stirred solution of indole-2-carboxaldehyde (284 mg, 1.96 mmol) in DMF (2.0 mL) was added benzyl amine (214 μL, 1.96 mmol). The reaction mixture was stirred for 3 hours before the addition of K$_2$CO$_3$ (270 mg, 1.96 mmol) and 1-(isocyanomethylsulfonyl)-4-methylbenzene (382 mg, 1.96 mmol). The reaction mixture was then heated to 60° C. and stirred for 24 hours before being quenched with H$_2$O (10 mL). The layers were separated and the aqueous phase was extracted with EtOAc (2×25 mL). The combined organic extracts were washed with brine, dried (MgSO$_4$) and concentrated in vacuo. Purification by column chromatography (MeOH 10% NH$_4$OH/CH$_2$Cl$_2$, 0:1→1:9 gradient run) provided compound 9b (319 mg, 1.17 mmol, 60%) as a white solid.

$^1$H NMR (acetone-d6, 300 MHz) δ 10.52 (s, 1H), 7.78 (s, 1H), 7.47 (d, J=8.5 Hz, 1H), 7.40-7.25 (m, 5H), 7.16-7.06 (m, 3H), 6.99 (t, J=7.4 Hz, 1H), 6.44 (s, 1H), 5.55 (s, 2H); $^{13}$C NMR (acetone-d6, 75 MHz): 140.8, 138.7, 137.6, 129.9, 129.7, 129.7, 129.5, 128.5, 128.3, 127.4, 122.8, 121.0, 120.5, 111.8, 101.0, 49.6; HRMS (ESI) calculated for C$_{18}$H$_{16}$N$_3$ [M+H]$^+$: 274.1339. Found: 274.1335. Purity by HPLC: 94% (t$_R$=8.80 min).

The following Series 1 inhibitors were prepared in an analogous manner to 2-(1-benzyl-1H-imidazol-5-yl)-1H-indole (9b):

Characterization of 2-(1-benzyl-1H-imidazol-5-yl)-5-bromo-1H-indole

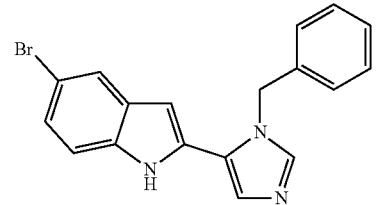 [SMILES: Brc1ccc2[nH]c(-c3cncn3Cc3ccccc3)cc2c1]

$^1$H NMR (acetone-d6, 300 MHz) δ 11.13 (s, 1H), 7.48 (s, 1H), 7.17 (d, J=1.8 Hz, 1H), 6.97 (s, 1H), 7.17-6.76 (m, 4H), 6.73 (dd, J=8.6, 1.9 Hz, 1H), 6.58 (d, J=7.2 Hz, 2H), 5.96 (s, 1H), 5.05 (s, 2H); HRMS (ESI) calculated for C$_{18}$H$_{15}$BrN$_3$ [M+H]$^+$: 352.0444. Found: 352.0443. Purity by HPLC: 97% (t$_R$=9.76 min). Isolated as a white solid (25.0 mg, 71.0 μmol, 16%).

Characterization of 2-(1-([1,1'-biphenyl]-4-ylmethyl)-1H-imidazol-5-yl)-5-bromo-1H-indole (9c)

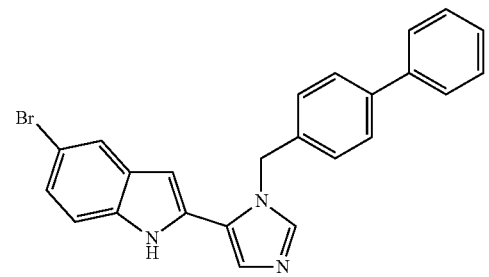 [SMILES: Brc1ccc2[nH]c(-c3cncn3Cc3ccc(-c4ccccc4)cc3)cc2c1]

$^1$H NMR (acetone-d6, 300 MHz) δ 10.75 (s, 1H), 7.87 (s, 1H), 7.67-7.61 (m, 5H), 7.48-7.41 (m, 3H), 7.38-7.32 (m, 2H), 7.26-7.17 (m, 3H), 6.53 (s, 1H), 5.61 (s, 2H); HRMS (ESI) calculated for C$_{24}$H$_{19}$BrN$_3$ [M+H]$^+$: 428.0757. Found: 428.0760. Purity by HPLC: 99% (t$_R$=9.22 min). Isolated as a yellow solid (66.0 mg, 154 μmol, 34% yield).

Characterization of 5-bromo-2-(1-(4-methoxybenzyl)-1H-imidazol-5-yl)-1H-indole (9d)

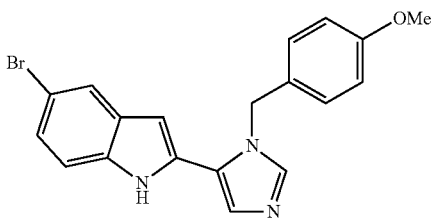 [SMILES: COc1ccc(Cn2cncc2-c2cc3cc(Br)ccc3[nH]2)cc1]

¹H NMR (acetone-d6, 300 MHz) δ 11.47 (s, 1H), 7.81 (s, 1H), 7.64 (d, J=1.8 Hz, 1H), 7.42 (s, 1H), 7.34 (d, J=8.6 Hz, 1H), 7.19 (dd, J=8.6, 1.8 Hz, 1H), 7.07 (d, J=8.6 Hz, 2H), 6.86 (d, J=8.6 Hz, 2H), 6.48 (s, 1H), 5.45 (s, 2H), 3.73 (s, 3H); HRMS (ESI) calculated for $C_{19}H_{17}BrN_3O$ [M+H]$^+$: 382.0550. Found: 382.0540. Purity by HPLC: 99% ($t_R$=9.89 min). Isolated as a white solid (110 mg, 288 μmol, 44% yield).

Characterization of 5-bromo-2-(1-(4-(trifluoromethyl)benzyl)-1H-imidazol-5-yl)-1H-indole (9e)

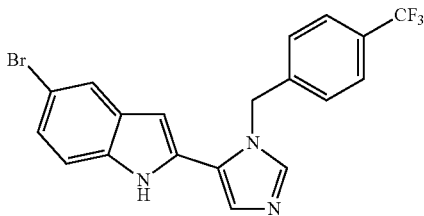 [SMILES: FC(F)(F)c1ccc(Cn2cncc2-c2cc3cc(Br)ccc3[nH]2)cc1]

¹H NMR (acetone-d6, 300 MHz) δ 10.82 (s, 1H), 7.91 (s, 1H), 7.70-7.64 (m, 3H), 7.36-7.32 (m, 3H), 7.34 (d, J=8.4 Hz, 1H), 7.24-7.19 (m, 1H), 6.45 (s, 1H), 5.70 (s, 2H); HRMS (ESI) calculated for $C_{19}H_{14}BrF_3N_3$ [M+H]$^+$: 420.0318. Found: 420.0303. Purity by HPLC: 98% ($t_R$=10.30 min). Isolated as a white solid (61.0 mg, 145 μmol, 16% yield).

Characterization of 4-((5-(5-bromo-1H-indol-2-yl)-1H-imidazol-1-yl)methyl)benzonitrile (9f)

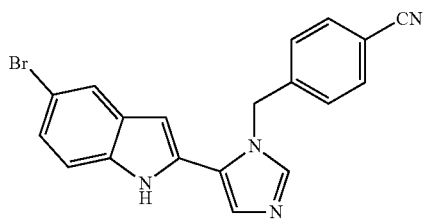 [SMILES: N#Cc1ccc(Cn2cncc2-c2cc3cc(Br)ccc3[nH]2)cc1]

¹H NMR (DMSO-d6, 300 MHz) δ 11.59 (s, 1H), 7.97 (s, 1H), 7.80-7.77 (m, 2H), 7.61 (s, 1H), 7.45 (s, 1H), 7.29 (d, J=8.8 Hz, 1H), 7.20-7.17 (m, 3H), 6.35 (s, 1H), 5.62 (s, 2H); HRMS (ESI) calculated for $C_9H_{14}BrN_4$ [M+H]$^+$: 377.0396. Found: 377.0383. Purity by HPLC: 96% ($t_R$=9.42 min). Isolated as a white solid (41.0 mg, 109 μmol, 12% yield).

Characterization of 5-bromo-2-(1-(piperidin-2-ylmethyl)-1H-imidazol-5-yl)-1H-indole (9g)

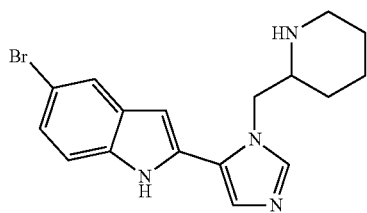 [SMILES: Brc1ccc2[nH]c(-c3cncn3CC3CCCCN3)cc2c1]

¹H NMR (acetone-d6, 300 MHz) δ 11.81 (br s, 1H), 7.74 (d, J=1.9 Hz, 1H), 7.72 (s, 1H), 7.39 (d, J=8.6 Hz, 1H), 7.27 (s, 1H), 7.23 (dd, J=8.7, 1.8 Hz, 1H), 6.64 (s, 1H), 4.26 (dd, J=14.2, 5.1 Hz, 1H), 4.08 (dd, J=14.3, 8.3 Hz, 1H), 3.11-3.06 (m, 1H), 3.03-2.94 (m, 1H), 2.57 (dt, J=11.6, 2.9 Hz, 1H), 1.82-1.68 (m, 2H), 1.62-1.57 (m, 1H), 1.50-1.15 (m, 3H); HRMS (ESI) calculated for $C_{17}H_{20}BrN_4$ [M+H]$^+$: 359.0866. Found: 359.0857. Purity by HPLC: 98% ($t_R$=7.73 min). (32.0 mg, 89.0 μmol, 20% yield).

Characterization of 2-(5-(5-bromo-1H-indol-2-yl)-1H-imidazol-1-yl)-1-phenylethan-1-ol (9h)

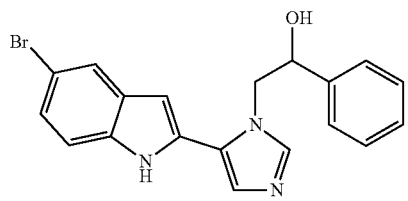 [SMILES: OC(Cn1cncc1-c1cc2cc(Br)ccc2[nH]1)c1ccccc1]

¹H NMR (acetone-d6, 300 MHz) δ 11.12 (s, 1H), 7.77 (s, 1H), 7.66 (s, 1H), 7.42 (dt, J=9.7, 4.7 Hz, 3H), 7.38-7.23 (m, 5H), 7.22 (s, 1H), 5.12 (dd, J=8.5, 3.8 Hz, 1H), 4.44 (dd, J=14.4, 3.9 Hz, 1H), 4.32 (dd, J=14.4, 8.6 Hz, 1H); HRMS (ESI) calculated for $C_{19}H_{17}BrN_3O$ [M+H]$^+$: 382.0550. Found: 382.0537. Purity by HPLC: 97% ($t_R$=9.53 min). Isolated as an orange solid (174 mg, 955 μmol, 68% yield).

Characterization of 2-((5-(5-bromo-1H-indol-2-yl)-1H-imidazol-1-yl)methyl)aniline (9i)

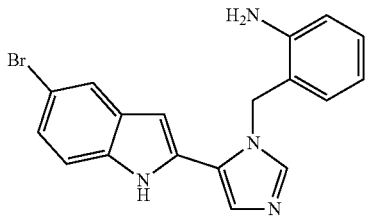 [SMILES: Nc1ccccc1Cn1cncc1-c1cc2cc(Br)ccc2[nH]1]

¹H NMR (acetone-d6, 300 MHz) δ 11.16 (s, 1H), 7.34 (s, 1H), 7.15 (s, 1H), 7.01 (s, 1H), 6.85 (d, J=8.4 Hz, 1H), 6.73 (d, J=8.6 Hz, 1H), 6.51 (d, J=6.6 Hz, 1H), 6.26 (d, J=7.9 Hz, 1H), 5.98 (s, 1H), 5.87-5.67 (m, 2H), 4.78 (d, J=7.6 Hz, 4H)); HRMS (ESI) calculated for $C_{18}H_{16}BrN_4$ [M+H]$^+$: 367.0553. Found: 367.0564. Purity by HPLC: 99% ($t_R$=9.09 min). Isolated as a white solid (130 mg, 354 μmol, 32% yield).

Synthesis of 2-((5-(5-bromo-1H-indol-2-yl)-1H-imidazol-1-yl)methyl)phenol (9j)

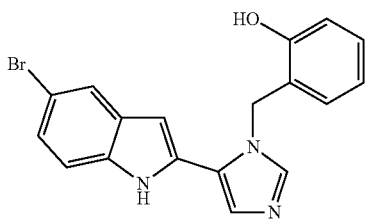 [SMILES: Oc1ccccc1Cn1cncc1-c1cc2cc(Br)ccc2[nH]1]

¹H NMR (DMSO-d6, 300 MHz) δ 11.65 (s, 1H), 9.99 (s, 1H), 7.80 (s, 1H), 7.63 (d, J=1.4 Hz, 1H), 7.44 (s, 1H), 7.32 (d, J=9.1 Hz, 1H), 7.18 (dd, J=8.6, 1.8 Hz, 1H), 7.10 (t, J=7.9 Hz, 1H), 6.89 (d, J=7.9 Hz, 1H), 6.89 (d, J=8.0 Hz, 1H), 6.68 (t, J=7.6 Hz, 1H), 6.52 (d, J=7.3 Hz, 1H), 6.40 (s, 1H), 5.37 (s, 2H); ¹³C NMR (DMSO-d6, 75 MHz) δ 154.5, 140.4, 135.0, 130.3, 128.9, 128.8, 128.6, 127.2, 125.2, 124.1, 123.3, 122.1, 119.2, 115.1, 112.9, 111.8, 98.4, 44.4; HRMS (ESI) calculated for $C_{18}H_{15}BrN_3O$ [M+H]⁺: 368.0393. Found: 368.0389. Purity by HPLC: 97% ($t_R$=9.44 min). Isolated as a white solid (97.0 mg, 264 μmol, 29% yield).

Characterization of 3-((5-(5-bromo-1H-indol-2-yl)-1H-imidazol-1-yl)methyl)phenol (9k)

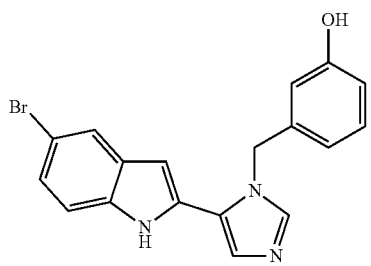 [SMILES: Oc1cccc(Cn2cncc2-c2cc3cc(Br)ccc3[nH]2)c1]

¹H NMR (acetone-d6, 300 MHz) δ 10.76 (s, 1H), 8.60 (s, 1H), 7.82 (s, 1H), 7.64 (s, 1H), 7.39 (s, 1H), 7.33 (d, J=8.6 Hz, 1H), 7.20 (dd, J=8.6, 1.9 Hz, 1H), 7.16 (t, J=8.2 Hz, 1H), 6.73 (dd, J=8.2, 2.4 Hz, 1H), 6.63 (dt, J=7.6, 0.7 Hz, 1H), 6.53 (s, 1H), 5.47 (s, 2H); HRMS (ESI) calculated for $C_{18}H_{15}BrN_3O$ [M+H]⁺: 368.0393. Found: 368.0381. Purity by HPLC: 95% ($t_R$=9.07 min). Isolated as a white solid (97.0 mg, 263 μmol, 30% yield).

Example 3—"Series 2" Inhibitors

The isolation of a byproduct from the van Leusen reaction between 5-bromo-2-indolecarboxaldeyde (7) and 2-hydroxybenzylamine during synthesis of inhibitor 9j. Upon close inspection of the reaction mixture, a second imidazole-containing compound was identified as a minor product (ca 2:1 ratio). After careful chromatographic separation, both products were analyzed using HSQC/HMBC spectroscopy. The structure of the minor product was assigned as 10c. While the major product of the reaction (9j) was found to have an activity of 6.0 μM, the byproduct 10c was found to have an activity of 180 nM (see below).

Without wishing to be bound by theory, molecular modelling of compound 10c revealed a proposed binding mode with the 2-hydroxyphenyl group now binding in pocket A, and the 5-bromoindole group now binding in pocket B. This flip in binding modes orientates the indole-NH in proximity to hydrogen bond with the propionate of the heme in IDO1. These so-called "flipped" compounds are hereafter referenced as "Series 2" inhibitors, and are identified herein using either 10 or G alphanumeric prefixes.

Computational docking indicated that the phenol ring of 10c now occupies pocket A and acts as a hydrogen bond donor to Ser167. The formation of compound 10c can be mechanistically-rationalized by tautomerization of intermediate 7i (likely promoted by the 2-phenolate group) to produce 7ii, as shown in the following scheme:

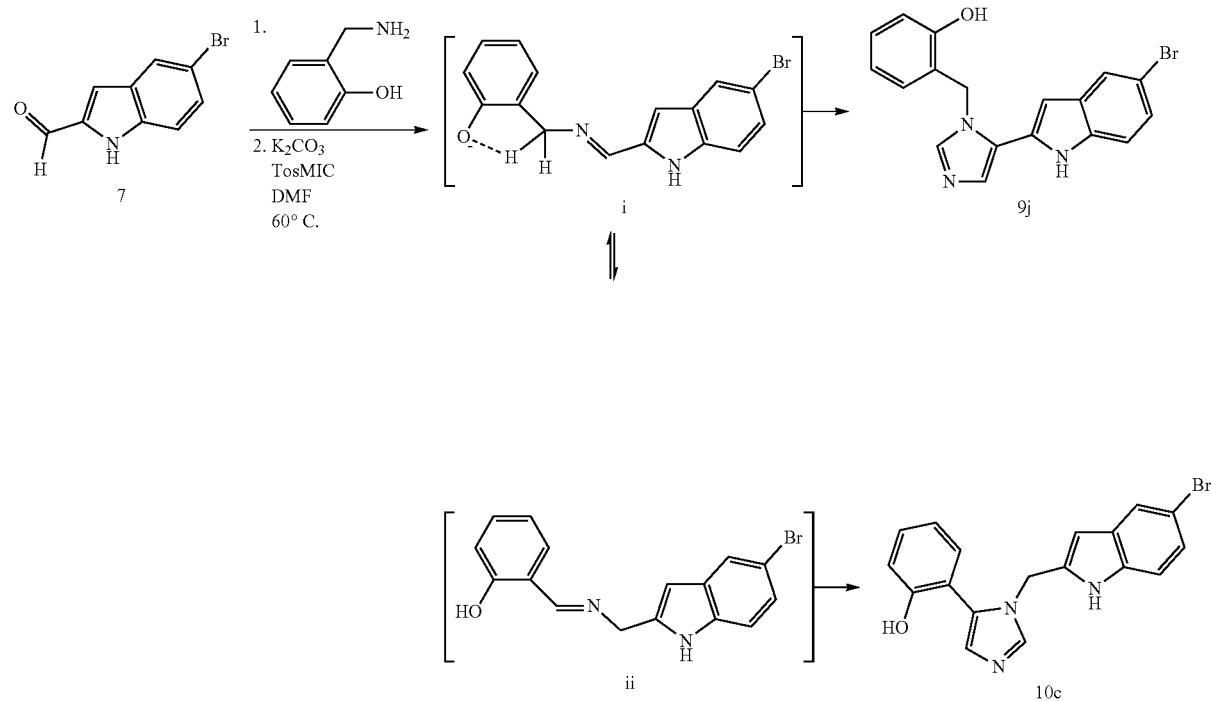

Series 2 inhibitors were prepared using the following general reaction scheme:

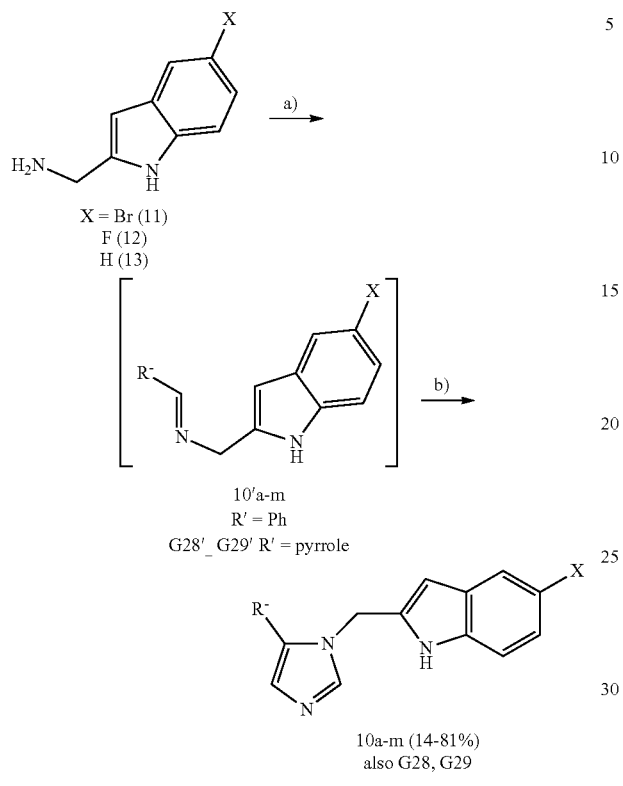

Synthesis and Characterization of (5-bromo-1H-indol-2-yl)methanamine (11)

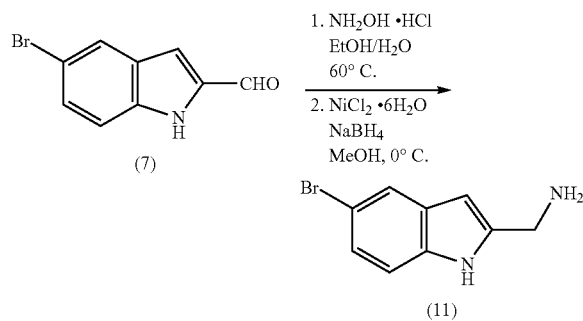

To a stirred solution of 5-bromo-1H-indole-2-carbaldehyde (7) (3.49 g, 15.6 mmol) in EtOH/H$_2$O (5:2, 70 mL) was added NH$_2$OH.HCl (2.15 g, 31.2 mmol) followed by Na$_2$CO$_3$ (2.48 mg, 23.4 mmol). The reaction mixture was heated to 60° C. and stirred for 1 h before being diluted with H$_2$O (25 mL). The layers were separated and the aqueous phase was extracted with EtOAc (2×50 mL). The combined organic extracts were washed with brine, dried (MgSO$_4$) and concentrated in vacuo. The crude residue was dissolved in MeOH (150 mL) and cooled to 0° C. NiCl$_2$.6H$_2$O (3.70 g, 15.6 mmol) was then added slowly followed by the slow addition of NaBH$_4$ (3.56 g, 93.6 mmol). The reaction mixture was stirred for 1 h before being quenched with H$_2$O (10 mL). The layers were separated and the aqueous phase was extracted with EtOAc (2×50 mL). The combined organic extracts were washed with brine, dried (MgSO$_4$) and concentrated in vacuo. Purification by column chromatography (MeOH 10% NH$_4$OH/CH$_2$Cl$_2$, 0:1→1:9 gradient run) provided the amine 11 (1.52 g, 6.76 mmol, 43%) as a brown solid.

$^1$H NMR (DMSO-d6, 300 MHz) δ 11.31 (br s, 1H), 7.63 (d, J=1.8 Hz, 1H), 7.32 (d, J=8.5 Hz, 1H), 7.14 (dd, (d, J=8.5, 1.9 Hz, 1H), 6.26 (s, 1H), 3.90 (s, 2H); $^{13}$C NMR (DMSO-d6, 75 MHz) δ 143.9, 134.8, 130.1, 122.7, 121.6, 112.8, 111.3, 97.6, 39.1.

Synthesis and Characterization of (5-fluoro-1H-indol-2-yl)methanamine (12)

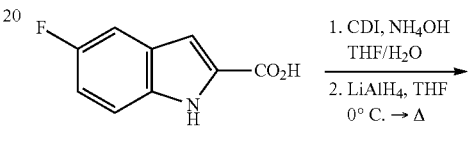

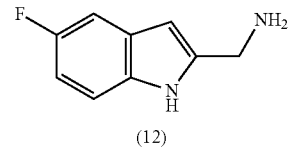

To a stirred solution of 5-Fluoroindole-2-carboxylic acid 14 (5.00 g, 27.8 mmol) in THF (150 mL) was added CDI (9.00 g, 55.8 mmol). The reaction mixture was stirred for 2 h before the addition of NH$_4$OH (28-30% aq. solution, 50 mL). The reaction mixture was then stirred for 2 h before being quenched with H$_2$O (100 mL). The layers were separated and the aqueous phase was extracted with EtOAc (2×100 mL). The combined organic extracts were washed with brine, dried (MgSO$_4$) and concentrated in vacuo. The crude residue was dissolved in THF (150 mL) and cooled to 0° C. LiAlH$_4$ (2.50 g, 65.9 mmol) was added slowly and the reaction mixture was warmed to RT before heating to reflux and stirred for 2 h. The reaction mixture was then quenched with H$_2$O (100 mL). The layers were separated and the aqueous phase was extracted with EtOAc (2×100 mL). The combined organic extracts were washed with brine, dried (MgSO$_4$) and concentrated in vacuo. Purification by column chromatography (MeOH 10% NH$_4$OH/CH$_2$Cl$_2$, 0:1→1:9 gradient run) provided the amine 12 (3.45 g, 21.0 mmol, 76%) as a white solid.

$^1$H NMR (DMSO-d6, 300 MHz) δ 11.7 (br s, 1H), 7.29 (dd, J=8.8, 4.5 Hz, 1H), 7.18 (d, J=10.1, 1.3 Hz, 1H), 6.83 (dt, J=9.2, 1.7 Hz, 1H), 6.23 (s, 1H), 3.84 (s, 2H); $^{13}$C NMR (DMSO-d6, 75 MHz) δ 156.8 (d, J(C, F)=229.9 Hz), 144.6, 132.7, 128.4 (d, J(C, F)=9.9 Hz), 111.6 (d, J(C, F)=9.5 Hz), 108.0 (d, J(C, F)=25.8 Hz), 104.0 (d, J(C, F)=23.2 Hz), 97.9 (d, J(C, F)=3.2 Hz), 48.4.

Synthesis and Characterization of 2-(1-((5-bromo-1H-indol-2-yl)methyl)-1H-imidazol-5-yl)phenol (10c)

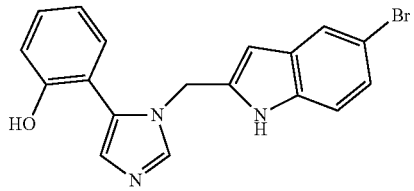 [SMILES: Oc1ccccc1-c1cncn1Cc1cc2cc(Br)ccc2[nH]1]

From 5-bromo-1H-indole-2-carbaldehyde (7) of Example 16: To a stirred solution of 5-bromo-1H-indole-2-carbaldehyde (7) (200 mg, 0.89 mmol) in DMF (2.0 mL) was added 2-(aminomethyl)phenol (110 mg, 0.89 mmol). The reaction mixture was stirred for 3 h before the addition of $K_2CO_3$ (246 mg, 1.78 mmol) and 1-(isocyanomethylsulfonyl)-4-methylbenzene (174 mg, 893 µmol). The reaction mixture was then heated to 60° C. and stirred for 24 hours before being quenched with $H_2O$ (5 mL). The layers were separated and the aqueous phase was extracted with EtOAc (2×25 mL). The combined organic extracts were washed with brine, dried ($MgSO_4$) and concentrated in vacuo. Purification by column chromatography (MeOH 10% $NH_4OH$/$CH_2Cl_2$, 0:1→1:9 gradient run) provided compound 10c (54.0 mg, 263 µmol, 16%) as a brown solid.

From (5-bromo-1H-indol-2-yl)methanamine (11) of Example 16: To a stirred solution of (5-bromo-1H-indol-2-yl)methanamine (11) (500 mg, 2.22 mmol) in DMF (2 mL) was added salicylaldehyde (236 µL, 2.22 mmol). The reaction mixture was stirred for 3 h before the addition of $K_2CO_3$ (591 mg, 4.44 mmol) and 1-(isocyanomethylsulfonyl)-4-methylbenzene (433 mg, 2.22 mmol). The reaction mixture was then heated to 60° C. and stirred for 24 hours before being quenched with $H_2O$ (5 mL). The layers were separated and the aqueous phase was extracted with EtOAc (2×25 mL). The combined organic extracts were washed with brine, dried ($MgSO_4$) and concentrated in vacuo. Purification by column chromatography (MeOH 10% $NH_4OH$/$CH_2Cl_2$, 0:1→1:9 gradient run) provided compound 10c (166 mg, 451 µmol, 20%) as a brown solid.

$^1$H NMR (DMSO-d6, 300 MHz) δ 11.28 (s, 1H), 9.87 (s, 1H), 7.75 (s, 1H), 7.56 (d, J=1.6 Hz, 1H), 7.26 (d, J=8.6 Hz, 1H), 7.21 (dd, J=11.5, 4.9 Hz, 2H), 7.13 (dd, J=8.6, 1.9 Hz, 1H), 7.07 (dd, J=7.5, 1.5 Hz, 1H), 6.98-6.92 (m, 1H), 6.87 (s, 1H), 6.79 (t, J=7.4 Hz, 1H), 5.78 (d, J=14.8 Hz, 1H), 5.26 (s, 2H); $^{13}$C NMR (DMSO-d6, 75 MHz) δ 155.0, 138.0, 136.9, 134.9, 131.8, 130.0, 129.8, 129.5, 127.8, 123.6, 122.0, 119.2, 116.7, 115.7, 113.1, 111.5, 99.6, 42.1; HRMS (ESI) calculated for $C_{18}H_{15}BrN_3O$ [M+H]$^+$: 368.0393. Found: 368.0406. Purity by HPLC: 95% ($t_R$=9.33 min).

The following compounds were synthesized following a procedure analogous to that for the synthesis of compound 10c:

Characterization of 2-((5-phenyl-1H-imidazol-1-yl)methyl)-1H-indole (10a)

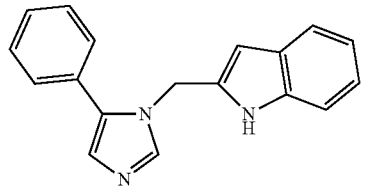 [SMILES: c1ccc(-c2cncn2Cc2cc3ccccc3[nH]2)cc1]

$^1$H NMR (acetone-d6, 300 MHz) δ 10.88 (s, 1H), 7.78 (s, 1H), 7.49-7.42 (m, 4H), 7.41-7.38 (m, 1H), 7.37-7.34 (m, 2H), 7.09-7.04 (m, 2H), 6.99-6.94 (m, 1H), 6.09 (s, 1H), 5.43 (s, 2H); $^{13}$C NMR (DMSO-d6, 75 MHz) δ 139.4, 136.4, 135.0, 132.5, 129.7, 128.8, 128.1, 127.7, 127.6, 121.3, 120.0, 119.1, 111.3, 100.0, 42.3; HRMS (ESI) calculated for $C_{18}H_{16}N_3$ [M+H]$^+$: 274.1339. Found: 274.1340. Purity by HPLC: 99% ($t_R$=10.37 min). Isolated as an orange solid (99.0 mg, 362 µmol, 18% yield).

Characterization of 5-bromo-2-((5-phenyl-1H-imidazol-1-yl)methyl)-1H-indole (10b)

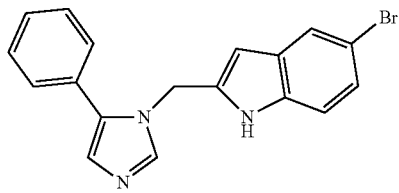 [SMILES: Brc1ccc2[nH]c(Cn3cncc3-c3ccccc3)cc2c1]

$^1$H NMR (acetone-d6, 300 MHz) δ 11.39 (br s, 1H), 7.85 (d, J=0.8 Hz, 1H), 7.61 (d, J=1.9 Hz, 1H), 7.42-7.32 (m, 5H), 7.29 (d, J=8.6 Hz, 1H), 7.16 (dd, J=8.6, 2.0 Hz, 1H), 7.09 (d, J=0.9 Hz, 1H), 5.95 (s, 1H), 5.40 (s, 2H); $^{13}$C NMR (DMSO-d6, 75 MHz) δ 139.5, 136.9, 135.0, 132.5, 129.6, 129.5, 128.8, 128.1, 127.8, 123.7, 122.1, 112.2, 111.6, 99.6, 42.3; HRMS (ESI) calculated for $C_{18}H_{15}BrN_3$ [M+H]$^+$: 352.0444. Found: 352.0443. Purity by HPLC: 99% ($t_R$=9.67 min). Isolated as a white solid (99.0 mg, 281 µmol, 14% yield).

Characterization of 2-(1-((5-bromo-1H-indol-2-yl)methyl)-1H-imidazol-5-yl)-4-fluorophenol (10d)

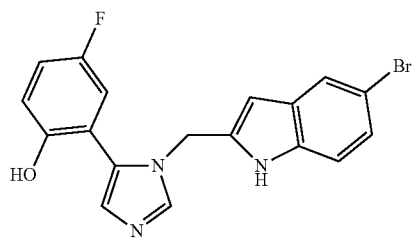 [SMILES: Oc1ccc(Cl)cc1-c1cncn1Cc1cc2cc(Br)ccc2[nH]1]

$^1$H NMR (DMSO-d6, 300 MHz) δ 10.37 (br s, 1H), 7.68 (d, J=0.7 Hz, 1H), 7.61 (d, J=1.9 Hz, 1H), 7.27 (d, J=8.7 Hz, 1H), 7.16 (dd, J=8.6, 1.9 Hz, 1H), 7.02 (dd, J=4.8, 2.8 Hz, 1H), 7.01 (d, J=5.3 Hz), 6.96 (d, J=0.8 Hz, 1H), 6.91 (d,

J=2.6 Hz, 1H), 6.89 (d, J=2.1 Hz, 1H), 6.12 (s, 1H), 5.40 (s, 2H); $^{13}$C NMR (DMSO-d6, 75 MHz) δ 156.1 (d, J(C, F)=234.7 Hz), 152.3, 139.4, 137.7, 135.9, 130.4, 129.9, 129.4, 124.6, 123.0, 118.7 (d, J(C, F)=8.8 Hz), 118.5 (d, J(C, F)=23.1 Hz), 117.5 (d, J(C, F)=8.1 Hz), 117.1 (d, J(C, F)=22.6 Hz), 114.1, 112.5, 100.6, 41.4; HRMS (ESI) calculated for $C_{18}H_{14}BrFN_3O$ [M+H]$^+$: 386.0304. Found: 386.0307. Purity by HPLC: 93% ($t_R$=9.29 min). Isolated as a white solid (120 mg, 311 µmol, 35% yield).

Characterization of 2-(1-((5-bromo-1H-indol-2-yl)methyl)-1H-imidazol-5-yl)-4-chlorophenol (10e)

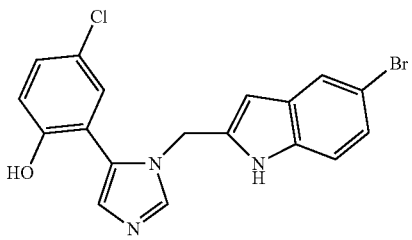

$^1$H NMR (DMSO-d6, 300 MHz) δ 10.99 (s, 1H), 10.03 (br s, 1H), 7.70 (d, J=0.8 Hz, 1H), 7.59 (d, J=1.8 Hz, 1H), 7.29 (d, J=8.6 Hz, 1H), 7.23 (dd, J=8.7, 2.7 Hz, 1H), 7.15 (dd, J=8.6, 1.9 Hz, 1H), 7.11 (d, J=2.7 Hz, 1H), 7.03 (d, J=8.7 Hz, 1H), 6.93 (d, J=0.8 Hz, 1H), 6.04 (s, 1H), 5.34 (s, 2H); $^{13}$C NMR (DMSO-d6, 75 MHz) δ 154.1, 138.5, 136.7, 134.9, 130.8, 129.4, 128.7, 128.4, 123.7, 122.4, 122.1, 118.6, 117.2, 113.2, 111.6, 99.7, 42.3; HRMS (ESI) calculated for $C_{18}H_{14}BrClN_3O$ [M+H]$^+$: 402.0003. Found: 402.0005. Purity by HPLC: 99% ($t_R$=9.55 min). Isolated as a white solid (148 mg, 368 µmol, 50% yield).

Characterization of 2-(1-((5-fluoro-1H-indol-2-yl)methyl)-1H-imidazol-5-yl)phenol (10f)

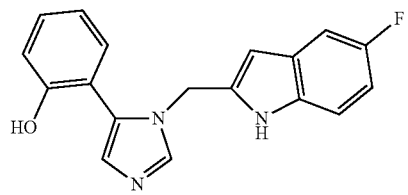 [SMILES: Oc1ccccc1-c1cncn1Cc1cc2cc(F)ccc2[nH]1]

$^1$H NMR (DMSO-d6, 300 MHz) δ 11.19 (br s, 1H), 9.99 (br s, 1H), 7.77 (d, J=0.96 Hz, 1H), 7.29 (d, J=8.8, 4.6 Hz, 1H), 7.26-7.20 (m, 1H), 7.15 (dd, J=10.0, 2.5 Hz, 1H), 7.10 (dd, J=7.5, 1.7 Hz, 1H), 6.98 (dd, J=8.1, 0.8 Hz, 1H), 6.90-6.83 (m, 2H), 6.80 (dd, J=7.5, 0.9 Hz, 1H), 5.83 (s, 1H), 5.27 (s, 2H); $^{13}$C NMR (DMSO-d6, 75 MHz) δ 157.0 (d, J(C, F)=231.1 Hz), 155.1, 138.0, 137.3, 132.9, 131.9, 130.2, 129.9, 127.9, 127.8, 119.2, 116.7, 115.7, 112.1 (d, J(C, F)=9.8 Hz), 109.3 (d, J (C, F)=26.2 Hz), 104.5 (d, J(C, F)=23.2), 100.2 (d, J(C, F)=4.6 Hz), 42.3; HRMS (ESI) calculated for $C_{18}H_{15}FN_3O$ [M+H]$^+$: 308.1194. Found: 308.1189. Purity by UPLC: 99% ($t_R$=1.79 min). Isolated as a white solid (326 mg, 1.06 mmol, 58% yield).

Characterization of 3-(1-((5-fluoro-1H-indol-2-yl)methyl)-1H-imidazol-5-yl)phenol (10g)

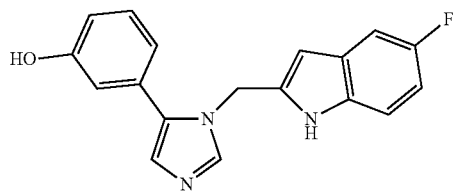 [SMILES: Oc1cccc(-c2cncn2Cc2cc3cc(F)ccc3[nH]2)c1]

$^1$H NMR (DMSO-d6, 300 MHz) δ 11.30 (br s, 1H), 9.64 (br s, 1H), 7.82 (s, 1H), 7.33 (dd, J=8.7, 4.8 Hz, 1H), 7.24-7.19 (m, 2H), 7.05 (s, 1H), 6.93-6.75 (m, 4H), 5.97 (s, 1H), 5.37 (s, 2H); $^{13}$C NMR (DMSO-d6, 75 MHz) δ 157.6, 157.0 (d, J(C, F)=231.3 Hz), 139.4, 137.3, 133.1, 132.7, 130.8, 129.9, 127.9 (d, J(C, F)=10.4 Hz), 127.5, 118.8, 115.0, 114.9, 112.2 (d, J(C, F)=9.7 Hz), 109.4 (d, J(C, F)=26.1 Hz), 104.6 (d, J(C, F)=23.6 Hz), 100.1 (d, J(C, F)=4.5 Hz), 42.3; HRMS (ESI) calculated for $C_{18}H_{15}FN_3O$ [M+H]$^+$: 308.1194. Found: 308.1208. Purity by UPLC: 98% ($t_R$=1.72 min). Isolated as a white solid (76.0 mg, 247 µmol, 14% yield).

Characterization of 4-(1-((5-fluoro-1H-indol-2-yl)methyl)-1H-imidazol-5-yl)phenol (10h)

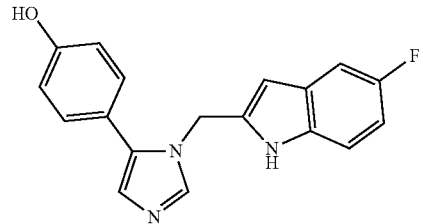 [SMILES: Oc1ccc(-c2cncn2Cc2cc3cc(F)ccc3[nH]2)cc1]

$^1$H NMR (DMSO-d6, 300 MHz) δ 11.26 (s, 1H), 9.67 (s, 1H), 7.77 (s, 1H), 7.31 (dd, J=8.7, 4.6 Hz, 1H), 7.19 (d, J=8.4 Hz, 1H), 7.18 (s, 1H), 6.94 (s, 1H), 6.89 (dt, J=9.5, 2.2 Hz, 1H), 6.79 (d, J=8.4 Hz, 1H), 5.96 (s, 1H), 5.30 (s, 1H), 5.30 (s, 2H); $^{13}$C NMR (DMSO-d6, 75 MHz) δ 157.3, 157.0 (d, J(C, F)=231.1 Hz), 138.6, 137.4, 133.0, 132.8, 129.8, 127.9 (d, J(C, F)=10.4 Hz), 126.7, 120.1, 115.6, 112.2 (d, J (C, F)=9.7 Hz), 109.4 (d, J(C, F)=26.0 Hz), 104.6 (d, J(C, F)=23.2 Hz), 100.2 (d, J (C, F)=4.4 Hz), 40.4; HRMS (ESI) calculated for $C_{18}H_{15}FN_3O$ [M+H]$^+$: 308.1194. Found: 308.1200. Purity by UPLC: 99% ($t_R$=1.51 min). Isolated as a white solid (267 mg, 869 µmol, 71% yield).

Characterization of 2-chloro-6-(1-((5-fluoro-1H-indol-2-yl)methyl)-1H-imidazol-5-yl)phenol (10i)

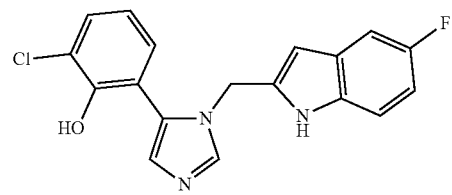 [SMILES: Oc1c(Cl)cccc1-c1cncn1Cc1cc2cc(F)ccc2[nH]1]

$^1$H NMR (DMSO-d6, 300 MHz) δ 11.16 (br s, 1H), 9.68 (br s, 1H), 7.82 (s, 1H), 7.41 (dd, J=8.0, 1.6 Hz, 1H), 7.27 (dd, J=8.8, 4.7 Hz, 1H), 7.14 (dd, J=10.0, 2.5 Hz, 1H), 7.04 (dd, J=7.6, 1.6 Hz, 1H), 6.93 (d, J=1.0 Hz, 1H), 6.90-6.81 (m, 2H), 5.84 (d, J=1.3 Hz, 1H), 5.22 (s, 2H); $^{13}$C NMR (DMSO-d6, 75 MHz) δ 157.0 (d, J(C, F)=231.2 Hz), 150.8, 138.6, 137.0, 132.9, 130.7, 130.1, 128.8, 128.4, 127.8 (d, J(C, F)=10.4 Hz), 121.5, 120.4, 119.9, 112.1 (d, J(C, F)=9.7 Hz), 109.3 (d, J(C, F)=20.6 Hz), 104.5 (d, J(C, F)=23.2 Hz), 100.2 (d, J(C, F)=4.0 Hz), 40.4; HRMS (ESI) calculated for $C_{18}H_{14}ClFN_3O$ [M+H]$^+$: 342.0804. Found: 342.0806. Purity by UPLC: 99% ($t_R$=1.67 min). Isolated as a white solid (193 mg, 565 μmol, 46% yield).

Characterization of 5-chloro-2-(1-((5-fluoro-1H-indol-2-yl)methyl)-1H-imidazol-5-yl)phenol (10j)

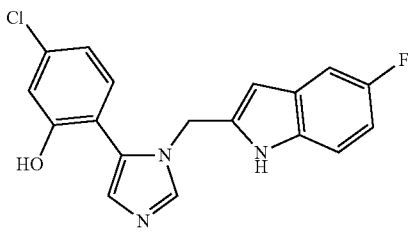 [SMILES: Oc1cc(Cl)ccc1-c1cncn1Cc1cc2cc(F)ccc2[nH]1]

$^1$H NMR (DMSO-d6, 300 MHz) δ 11.20 (s, 1H), 10.57 (br s, 1H), 7.80 (s, 1H), 7.29 (dd, J=8.8, 4.7 Hz, 1H), 7.16 (dd, J=10.1, 2.1 Hz, 1H), 7.10 (d, J=8.1 Hz, 1H), 7.00 (d, J=1.8 Hz, 1H), 6.92 (s, 1H), 6.91-6.84 (m, 2H), 5.88 (s, 1H), 5.26 (s, 2H); $^{13}$C NMR (DMSO-d6, 75 MHz) δ 157.0 (d, J(C, F)=231.7 Hz), 156.1, 138.4, 137.1, 133.7, 133.1, 132.9, 128.9, 127.9 (d, J(C, F)=10.6 Hz), 127.8, 119.2, 116.0, 115.5, 112.2 (d, J(C, F)=9.7 Hz), 109.3 (d, J(C, F)=26.0 Hz), 104.5 (d, J(C, F)=23.2 Hz), 100.2 (d, J(C, F)=4.5 Hz), 42.4; HRMS (ESI) calculated for $C_{18}H_{14}ClFN_3O$ [M+H]$^+$: 342.0804. Found: 342.0810. Purity by UPLC: 99% ($t_R$=1.88 min). Isolated as a white solid (315 mg, 922 μmol, 50% yield).

Characterization of 3-chloro-2-(1-((5-fluoro-1H-indol-2-yl)methyl)-1H-imidazol-5-yl)phenol (10k)

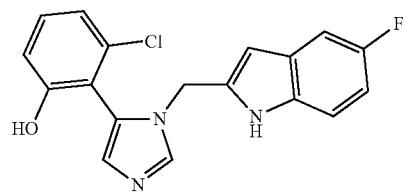 [SMILES: Oc1cccc(Cl)c1-c1cncn1Cc1cc2cc(F)ccc2[nH]1]

$^1$H NMR (DMSO-d6, 300 MHz) δ 11.16 (br s, 1H), 10.18 (br s, 1H), 7.83 (d, J=0.9 Hz, 1H), 7.27 (dd, J=8.9, 4.8 Hz, 1H), 7.23 (t, J=8.1 Hz, 1H), 7.12 (dd, J=10.1, 2.4 Hz, 1H), 6.94-6.82 (m, 4H), 5.80 (br s, 1H), 5.16 (d, J=16.1 Hz, 1H), 5.02 (d, J=16.0 Hz, 1H); $^{13}$C NMR (DMSO-d6, 75 MHz) δ 157.7, 156.9 (d, J(C, F)=231.2 Hz), 138.0, 136.7, 135.3, 132.9, 130.9, 128.9, 127.8 (d, J(C, F)=10.1 Hz), 125.5, 119.8, 115.8, 114.3, 112.0 (d, J(C, F)=9.5 Hz), 109.2 (d, J(C, F)=25.9 Hz), 104.4 (d, J(C, F)=23.0 Hz), 100.2 (d, J(C, F)=3.6 Hz), 42.0; HRMS (ESI) calculated for $C_{18}H_{14}ClFN_3O$ [M+H]$^+$: 342.0804. Found: 342.0813. Purity by UPLC: 99% ($t_R$=1.64 min). Isolated as a white solid (345 mg, 1.01 mmol, 81% yield).

Characterization of 4-fluoro-2-(1-((5-fluoro-1H-indol-2-yl)methyl)-1H-imidazol-5-yl)phenol (10l)

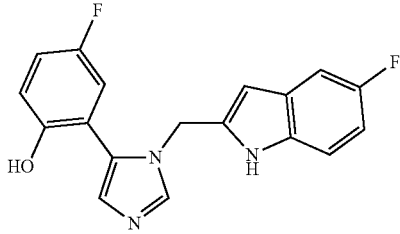

$^1$H NMR (DMSO-d6, 300 MHz) δ 11.20 (s, 1H), 10.01 (s, 1H), 7.79 (s, 1H), 7.29 (dd, J=8.8, 4.6 Hz, 1H), 7.16 (dd, J=10.0, 2.4 Hz, 1H), 7.07 (dt, J=8.3, 3.1 Hz, 1H), 6.98-6.91 (m, 3H), 6.87 (dt, J=9.3, 2.2 Hz, 1H), 5.87 (s, 1H), 5.30 (s, 2H); $^{13}$C NMR (DMSO-d6, 75 MHz) δ 157.6 (J(C, F)=137.6 Hz), 154.4 (J(C, F)=141.1 Hz), 151.4 (J(C, F)=1.6 Hz), 138.5, 137.1, 132.9, 129.0 (J(C, F)=1.6 Hz), 128.4, 127.8 (J(C, F)=10.4 Hz), 117.8 (J(C, F)=9.4 Hz), 117.6 (J(C, F)=23.7 Hz), 116.6 (J(C, F)=8.2 Hz), 116.1 (J(C, F)=22.8 Hz), 112.2 (J(C, F)=9.7 Hz), 109.3 (J(C, F)=26.1 Hz), 104.6 (J(C, F)=23.2 Hz), 100.3 (J(C, F)=4.5 Hz), 42.4; HRMS (ESI) calculated for $C_{18}H_{14}F_2N_3O$ [M+H]$^+$: 326.1099. Found: 326.1104. Purity by UPLC: 99% ($t_R$=1.80 min). Isolated as a white solid (380 mg, 1.17 mmol, 63% yield).

Characterization of 2-((5-(1H-pyrrol-2-yl)-1H-imidazol-1-yl)methyl)-5-bromo-1H-indole (G28)

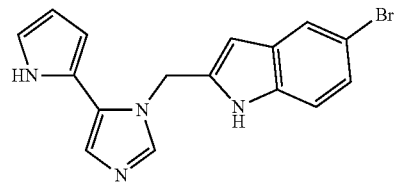 [SMILES: Brc1ccc2[nH]c(Cn3cncc3-c3ccc[nH]3)cc2c1]

$^1$H NMR (acetone-d6, 300 MHz) δ 10.94 (br s, 1H), 10.67 (br s, 1H), 7.29 (s, 1H), 7.17 (br s, 1H), 6.86 (d, J=8.8 Hz, 1H), 8.39 (d, J=8.7 Hz, 1H), 6.63 (s, 1H), 6.37 (br s, 1H), 5.60 (s, 1H), 5.51 (s, 1H), 4.96 (s, 1H); HRMS (ESI) calculated for $C_{16}H_{14}BrN_4$ [M+H]$^+$: 341.0396. Found: 341.0371.

Characterization of 2-((5-(1H-pyrrol-2-yl)-1H-imidazol-1-yl)methyl)-5-fluoro-1H-indole (G29)

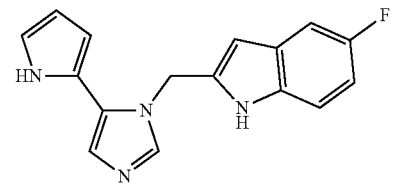 [SMILES: Fc1ccc2[nH]c(Cn3cncc3-c3ccc[nH]3)cc2c1]

$^1$H NMR (acetone-d6, 300 MHz) δ 11.27 (br s, 1H), 11.13 (br s, 1H), 7.74 (s, 1H), 7.32 (dd, J=8.8, 4.5 Hz, 1H), 7.19 (dd, J=9.9, 2.5 Hz, 1H), 7.08 (d, J=0.89, 1H), 6.89 (dt, J=9.3, 2.1 Hz, 1H), 6.83-6.81 (m, 1H), 6.07 (br s, 1H), 5.97 (br s, 1H), 5.40 (s, 1H); HRMS (ESI) calculated for $C_{16}H_{14}FN_4$ [M+H]$^+$: 281.1202. Found: 281.1212.

Characterization of 4-chloro-2-(1-((5-fluoro-1H-indol-2-yl)methyl)-1H-imidazol-5-yl)phenol (10m)

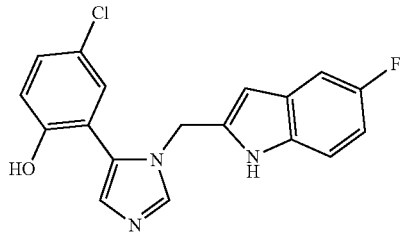

$^1$H NMR (DMSO-d6, 300 MHz) δ 11.17 (s, 1H), 10.24 (s, 1H), 7.76 (s, 1H), 7.30-7.24 (m, 2H), 7.15 (d, J=10.0, 2.28 Hz, 1H), 7.09 (d, J=7.67 Hz, 1H), 6.96 (d, J=8.7 Hz, 1H), 6.93 (d, J=0.8 Hz, 1H), 6.86 (dt, J=9.2, 2.3 Hz, 1H), 5.87 (s, 1H), 5.24 (s, 2H); $^{13}$C NMR (DMSO-d6, 75 MHz) δ 157.0 (d, J(C, F)=231.4 Hz), 154.1, 138.5, 137.0, 132.9, 130.8, 129.5, 128.7, 128.4, 127.8 (d, J(C, F)=10.4 Hz), 122.4, 118.6, 117.3, 112.2 (d, J(C, F)=9.7 Hz), 109.3 (d, J(C, F)=26.3 Hz), 104.5 (d, J(C, F)=23.3 Hz), 100.3 (d, J(C, F)=4.1 Hz), 42.4; HRMS (ESI) calculated for $C_{18}H_{14}ClFN_3O$ [M+H]$^+$: 342.0809. Found: 342.0809. Purity by UPLC: 99% ($t_R$=1.69 min). Isolated as a white solid (300 mg, 878 μmol, 72% yield).

Example 4—Biological Studies

A. Human Recombinant IDO1 Expression and Purification

*E. Coli* were transformed with a PET15b-6HISIDO1 vector. A single colony was inoculated in Luria-Bertani (LB) medium containing 100 ug/mL ampicillin and was allowed to grow for 4 hrs at 37° C. This culture was added to a 50 mL culture and grown overnight at 37° C. The 50 mL overnight culture was transferred to 1 L culture of LB Overnight Express™ autoinduction medium containing 635 μM Aminolevulinic acid, 20 μM Hematin porcine, and 100 ug/mL of ampicillin. 1 L culture was grown at 30° C. for 24 hours. Bacterial cells were then collected as a pellet through centrifugation at 6000 g for 10 min at 4° C. Cell Pellets were stored at −80° C. until use. Cell pellets corresponding to 500 mL of bacterial culture were suspended in 50 mM NaH$_2$PO$_4$, 300 mM NaCl, 10 mM imidazole, 0.1% Triton X-100, pH 7.8, 1 mg/mL Lysozyme (Sigma-Aldrich cat#L7001) and 1 tablet cOmplete™ EDTA-free Protease Inhibitor Cocktail per 50 mL of buffer (Roche cat #11873580001). The cell suspension was sonicated on ice at 90% maximal power using a Sonics Vibra-Cell VCX130 for 5 mins 30 seconds, then centrifuged at 16,000 g for 20 mins at 4° C. Supernatant was then collected and applied to 1 mL resin volume of cOmplete™ His-Tag Purification Resin (Roche cat#05893682001). The resin was washed with 20 resin volumes of 50 mM NaH$_2$PO$_4$, 300 mM NaCl, and 20 mM imidazole at pH 7.8. Protein containing fractions were collected in 1 mL fractions following addition of elution buffer (50 mM NaH$_2$PO$_4$, 300 mM NaCl and 500 mM imidazole at pH 8.0) to the resin. Protein containing fractions as determined by Bradford assay were then pooled and dialyzed into 50 mM Tris pH 7.5 buffer.

B. IDO1 Enzymatic Inhibition Assay

IDO enzymatic assay was carried out generally following a procedure provided in Röhrig, U. F.; Majjigapu, S. R.; Vogel, P.; Zoete, V.; Michielin, O., *J. Med. Chem.* 2015, 58 (24), 9421-37. A standard reaction mixture (200 μL/well) containing 50 mM potassium phosphate buffer (pH 6.5), 20 mM ascorbic acid (neutralised with NaOH), 200 μg/mL catalase, 10 μM methylene blue, 6.25 μg/mL recombinant human IDO1 and 200 μM L-Tryptophan was added to the test compound dissolved in DMSO at a determined concentration. The mixture was incubated for 1 hour at 37° C. and the reaction was stopped by adding 40 μL/well of 30% (w/v) trichloroacetic acid. After heating at 65° C. for 15 min, 125 μL was transferred into a well of a 96-well microplate and mixed with 125 μL of 2% (w/v) p-dimethylaminobenzaldehyde in acetic acid. The yellow pigment derived from kynurenine was measured at 480 nm using a Cytation™ 3 microplate reader. Percent inhibition was calculated using [(X−Y)/X]×100 where X is absorbance value of without inhibitor and Y is the absorbance value of enzyme with indicated concentration of inhibitor. Normalized data was analyzed with Graphpad Prism 6 using non-liner regression curve fitting. IC$_{50}$ values presented as means with N≥3.

| Entry | IC50 (μM) |
|---|---|
| 9a | 13.0 |
| 9b | 34.0 |
| 9c | 34.0 |
| 9d | 21.0 |
| 9e | >100 |
| 9f | 4.0 |
| 9g | >100 |
| 9h | 19.0 |
| 9i | 50.0 |
| 9j | 6.0 |
| 9k | 2.0 |
| 10a | 4.44 |
| 10b | 1.25 |
| 10c | 0.180 |
| 10d | 0.100 |
| 10e | 0.038 |
| 10f | 0.322 |
| 10g | 4.64 |
| 10h | 83.3 |
| 10i | 22.7 |
| 10j | 21.0 |
| 10k | 44.8 |
| 10l | 0.113 |
| 10m | 0.034 |
| G28 | 0.309 |
| G29 | 0.230 |

C. TDO2 Enzymatic Inhibition Assay

A standard reaction mixture (200 μL/well) containing 50 mM potassium phosphate buffer (pH 6.5), 20 mM ascorbic acid (neutralised with NaOH), 200 μg/mL catalase, 10 μM methylene blue, 12.5 μg/mL recombinant human IDO1 and 500 μM L-Tryptophan was added to the test compound dissolved in DMSO at a determined concentration. The mixture was incubated for 1 hour at 37° C. and the reaction was stopped by adding 40 μL/well of 30% (w/v) trichloroacetic acid. After heating at 65° C. for 15 min, 125 μL was transferred into a well of a 96-well microplate and mixed with 125 μL of 2% (w/v) p-dimethylaminobenzaldehyde in acetic acid. The yellow pigment derived from kynurenine was measured at 480 nm using a Cytation™ 3 microplate reader. Percent inhibition was calculated using [(X−Y)/X]×

100 where X is absorbance value of without inhibitor and Y is the absorbance value of enzyme with indicated concentration of inhibitor. Normalized data was analyzed with Graphpad Prism 6 using non-liner regression curve fitting. $IC_{50}$ values presented as means with N≥3.

| Compound | TDO $IC_{50}$ |
|---|---|
| 10l | 84.0 μM |
| 10m | 54.4 μM |
| 10f | >200 μM |
| 10e | >200 μM |
| 10c | 157.6 μM |
| 10d | 70.1 μM |
| 10b | >200 μM |
| 10g | 42.5 μM |

D. Cellular Assay of IDO1 Inhibition

Construction of Human IDO1 Inducible Expression Vector and HEK293 Cell Line

To generate the inducible expression vector, human IDO1 cDNA was PCR amplified using a validated IDO1 expression plasmid as template (Origene, cat#SC126221) and sub-cloned into TRIPZ Tet-On inducible expression vector (Dharmacon). Briefly, TRIPZ vector was digested with AgeI and MluI restriction enzymes and the vector backbone was recovered. IDO1 coding sequence was PCR cloned with forward primer containing AgeI and reverse primer containing MluI restriction site. Primer sequences are: IDO1 Fw 5'-GTCAACCGGTATGGCACACGCTATGGAAAACTC-3' and IDO1 Re 5'-GTCA ACGCGTTTAACCTTCCTT-CAAAAGGGATT-3'. PCR product was digested with AgeI and MluI then ligated with pre-cut TRIPZ vector. Cloning was confirmed by DNA sequencing. HEK-293 cell line was maintained in DMEM (high glucose) supplemented with 5% heat-inactivated Fetal Bovine Serum (GIBCO) and Antibiotic-Antimycotic (Life Technologies). Cells were grown at 37° C. in 5% C02 atmosphere. HEK-293 cells were transfected with TRIPZ vector carrying human IDO1 gene using Lipofectamine 2000 according to manufacturer's instruction. Stable cell lines (HEK293/TRIPZ-IDO1) were selected by growing cells in the presence of puromycin (1 ug/ml) for one week and then maintained in regular growth medium.

IDO1 Inhibition in HEK293/IDO1 Transfected Cells

HEK293/TRIPZ-IDO1 cells were seeded in a 96-well microplate at a density of $3 \times 10^4$ cells/well. 24 hours later, cell culture medium was added in the following order: first, 50 μL of complete medium with serial dilutions of compounds was added to cells and incubated for 30 min; second, 20 μL of complete medium containing 1 ug/ml doxycycline (Clontech) was added to each well for the induction of IDO1 expression. Cell culture medium was collected 24 h after the induction of IDO1. Medium was centrifuged at 3000 g for 15 min to sediment cell debris and 150 μL of supernatant was transferred to wells of new microplates. 30 μL of 30% (w/v) trichloroacetic acid was added to each sample-containing well and reaction was incubated at 65° C. for 20 min to hydrolyze N-formylkynurenine produced by the catalytic reaction of IDO1. The reaction mixture was centrifuged at 3000 g for 15 min. 125 μL of supernatant was transferred to a new assay plate and mixed with 125 μL of 2% (w/v) p-dimethylaminobenzaldehyde (Sigma-Aldrich cat#156477) in acetic acid. The yellow pigment derived from kynurenine was measured at 480 nm using a Cytation™ 3 microplate reader (BioTek). Percent inhibition was calculated using $[(X-Y)/X] \times 100$ where X is absorbance value of without inhibitor and Y is the absorbance value of enzyme with indicated concentration of inhibitor. Data was analyzed with Graphpad Prism 6 using non-linear regression curve fitting with $EC_{50}$ values presented as means with N≥3.

| Entry | EC50 (μM) |
|---|---|
| 9a | 11.0 |
| 9b | 11.0 |
| 9c | 3.10 |
| 9d | 4.30 |
| 9e | 4.50 |
| 9f | 6.90 |
| 9g | 10.7 |
| 9h | 9.50 |
| 9i | 12.0 |
| 9j | 5.0 |
| 9k | 10.0 |
| 10a | 9.12 |
| 10b | 18.7 |
| 10c | 1.45 |
| 10d | 1.04 |
| 10e | 0.890 |
| 10f | 0.480 |
| 10g | 4.19 |
| 10h | 4.56 |
| 10i | 6.26 |
| 10j | 5.55 |
| 10k | 6.40 |
| 10l | 0.320 |
| 10m | 0.260 |
| G28 | 0.467 |
| G29 | 0.250 |

Summary of Results

Compound 9a with a phenyl substituent linked by a methylene group was found to possess an IC50 of 13 μM: a two-fold increase in potency versus compound 6. The analogous nor-bromine compound 9b was found to be three-fold less active (IC50=34 μM). However, both compounds exhibited equivalent potency in cellular assay (EC50 11.0 μM). Further studies were performed to consider the effect of substituents positioned in the para-position of 9a to increase potency by either interacting with arginine-231 or by making hydrophobic interactions with additional residues in pocket B. Compounds 9c and 9e containing a 4-phenyl and 4-trifluoromethyl substituent respectively, displayed poorer activity against IDO1, while the electron rich 4-methyoxyphenyl compound 9d displayed a modest potency increase compared to the parent 9a. Compound 9f with a 4-cyano substituent showed ca 3-fold increase in potency relative to 9a. With an N3-substituent capable of binding in pocket B identified, the next objective was to increase the potency of the inhibitor series by addition of a H-bond donor. Inclusion of a hydrogen bond donor in either the ortho or meta positions of 9a was expected to provide opportunity for an intermolecular hydrogen bond to the propionate. Installation of a hydrogen bond donor (amine or hydroxyl) at the ortho-position of 9a afforded differing effects on the inhibitory activity. The 2-hydroxyphenyl derivative (9j) displayed an activity of 6 μM.

The most potent of Series 1 was found to be the 3-hydroxy substituted 9k with an activity of 2 μM. The modest potency jumps from the installation of the 4-cyano (9f) and 3-hydroxyl (9k) groups versus compound 9a were encouraging.

Further SAR studies were performed on the Series 2 inhibitors. The nor-hydroxyl analog 10b and was found to be approximately five-fold less active than compound 10c. While the nor-hydroxyl/nor-bromo analogue 10a displayed a 24-fold drop in potency. Based on literature precedent and the computation model employed in these studies, inclusion of substituents at the 5-position of the aromatic ring of 10c appeared optimal to interact with a small pocket at the top of the enzyme active site near cysteine-129. Compounds 10d and 10e were synthesized containing 5-fluoro- and 5-chloro substituents, respectively. Both analogs were found to be active in the nanomolar range.

Compound 10d displayed an inhibitory activity of 100 nM while the chloro-compound 10e displayed an activity of 38 nM. In an effort to reduce lipophilicity and improve ligand efficiency, the possibility of switching to a 5-fluoroindole ring was investigated. To that end, compounds 10f-m were synthesized starting from known amine 11 as outlined in the Examples above. Compounds 10f, 10l and 10m displayed comparable IDO $IC_{50}$ values relative to their brominated analogs (10c, 10d and 10e respectively). Compound 10m proved to be especially potent (IDO $IC_{50}$ 34 nM, IDO $EC_{50}$ 260 nM). Compound 10m is at least one-fold more potent in a head-to-head enzymatic assay than clinical candidate epacadostat. Intriguingly, switching to the 5-fluoroindole analogs had a beneficial effect on the relative $IC_{50}/EC_{50}$ values. While 5-bromoindole analogs (10b-e) displayed a significant reduction in potency in the cellular (HEK293) assays relative to the enzymatic assays, the 5-fluoroindole derivatives showed significant improvement in relative $IC_{50}/EC_{50}$ values.

Compounds 10l and 10m displayed excellent selectivity over TDO (84.0 μM and 54.4 μM respectively). Compounds 10a-g and 10l-m displayed good LE values (LE>0.3). Inhibitor 10m showed an LE value (0.44) which is comparable to the mean LE value (0.45) reported for oral drugs. 10f ($f_{u,plasma}$=4.03%) and 10l ($f_{u,plasma}$=1.64%) were identified as compounds with acceptable free fraction in plasma. In general, fluorinated analogs displayed higher $f_{u,plasma}$ values, likely due to reduced lipophilicity relative to the brominated analogs.

Example 5—Pharmacokinetics Studies

In order to assess the pharmacokinetics of the IDO1 inhibitors of the present application, two inhibitors were administered to mice at 20 mg/kg via PO (G29), or IP (G28). For a preliminary pharmacokinetic profile, three animals were sacrificed per time point at 30 minutes and two hours post-dose. For a full pharmacokinetic profile, three animals were sacrificed per time point at 15 minute, 30 minutes, 1, 2, 4, 6, 8, and 24 hours post-dose.

Blood samples were collected via cardiac puncture, the mice were perfused with phosphate buffered saline (PBS) and the brains were collected. The blood and brain samples were protein precipitated with ice-cold acetonitrile and the concentration of the test compound in the resulting supernatant was quantified using LC/MS/MS. For the full pharmacokinetic profile, the parameters were computed using the "PK" package with the R statistical computing software using a non-compartmental analysis.

Tissue Protein Binding:

The plasma and brain protein binding of compounds was determined using pooled plasma from mice (in-house) or pooled brain homogenized with PBS (1:3 m:v). We used the HTD 96b micro-equilibrium dialysis apparatus (HTDialysis, Gales Ferry Conn.), a 96 well teflon plate with wells bisected by a dialysis membrane with a molecular weight cutoff of 12-14 kilodaltons. One side of the well was loaded with tissue (plasma or brain) containing the test compound (150 μL) and the other side with phosphate buffer (150 μL). The apparatus was then incubated at 37° C. rotating at 100 rpm for 6 hours. After incubation, an aliquot from each side of the well was mixed with either buffer or plasma to ensure all collected samples had an equal mixture of tissue and buffer. The samples were then protein precipitated with ice-cold acetonitrile containing an internal standard (tolbutamide), centrifuged, and the supernatant was analyzed for the test compound by LC/MS/MS. Protein binding was determined by comparing the peak area for the test compound in the tissue and buffer samples.

The results of the full pharmacokinetic study using G28 are provided in the tables below:

| | Tissue Concentration | | | |
|---|---|---|---|---|
| | Plasma (mg/ml) | | Brain (ng/g) | |
| Time (hr) | Mean | SE | Mean | SE |
| 0.25 | 1,883 | 85 | 1,655 | 326 |
| 0.5 | 1,840 | 37 | 4,021 | 243 |
| 1 | 1,408 | 124 | 3,516 | 1,096 |
| 2 | 562 | 104 | 2,763 | 177 |
| 4 | 133 | 71 | 1,370 | 342 |
| 6 | BQL | | 552 | 85 |
| 8 | BQL | | 509.6 | 64.8 |

| Compound Parameters | | |
|---|---|---|
| Parameter Name | Plasma | Brain |
| $T_{max}$ (hr) | 0.25 | 0.5 |
| $C_{max}$ (ng/ml) | 1,883 | 4,021 |
| $T_{1/2}$ (hr) | 0.83 | 2.36 |
| $AUC_{0-last}$ (ng · h/mL) | 2,914 | 9,867 |
| $AUC_{0-\infty}$ (ng · h/mL) | 2,915 | 14,210 |
| % FU | 1.17% | 1.61% |
| $IC_{50}$ | 310 nM | |
| $EC_{50}$ | 470 nM | |

The results of the preliminary pharmacokinetic study using G29 are provided in the table below:

| Time (Hr) | Type | M1 | M2 | M3 | Mean (ng/ml) | SD |
|---|---|---|---|---|---|---|
| 0.5 | Plasma | 2658.6 | 1606.0 | 2740.2 | 2334.9 | 632.6 |
| | Brain | 2392.7 | 868.8 | 2561.5 | 1941.0 | 932.3 |
| | B/P Ratio | 0.9 | 0.5 | 0.9 | 0.8 | 0.2 |

| Time (Hr) | Type | M4 | M5 | M6 | Mean (ng/ml) | SD |
|---|---|---|---|---|---|---|
| 2 | Plasma | 628.9 | 408.4 | — | 518.6 | 156.0 |
| | Brain | 3447.9 | 2049.2 | — | 2748.6 | 989.0 |
| | B/P Ratio | 5.5 | 5.0 | — | 5.3 | 0.3 |

The results of these studies demonstrate that these IDO inhibitors are brain penetrant.

All publications, patents and patent applications mentioned in this Specification are indicative of the level of skill of those skilled in the art to which this invention pertains and are herein incorporated by reference to the same extent as if each individual publication, patent, or patent applications was specifically and individually indicated to be incorporated by reference.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

INCORPORATION OF SEQUENCE LISTING

Incorporated herein by reference in its entirety is the Sequence Listing for the application. The Sequence Listing is disclosed on a computer-readable ASCII text file titled, "Sequence_Listing_750-5PCTUS.txt", created on Jul. 8, 2020. The sequence_listing.txt file is 707 bytes in size.

The invention claimed is:

1. A compound, or a pharmaceutically acceptable salt thereof, of either Formula Ia or Formula Ib:

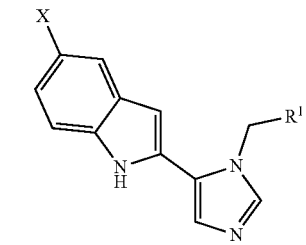

(Ia)

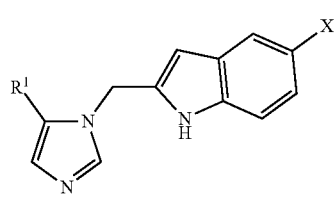

(Ib)

in which
X is H, F, Cl, or Br;
$R^1$ is piperidin-2-yl, 1-phenylmethan-1-yl-1-ol, pyrrol-2-yl, or

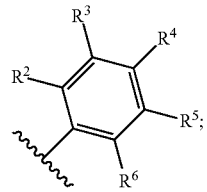

and $R^2$, $R^3$, $R^4$, $R^5$, and $R^6$ are each independently H, F, Cl, amino, hydroxy, alkoxy, cyano, trifluoromethyl, or phenyl.

2. The compound of claim 1, wherein $R^1$ is

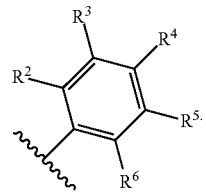

3. The compound of claim 2, wherein $R^4$ is H, F, Cl, amino, hydroxy, alkoxy, cyano, trifluoromethyl, or phenyl; and $R^2$, $R^3$, $R^5$, and $R^6$ are each independently H, F, Cl, amino, or hydroxy.

4. The compound of claim 3, wherein $R^4$ is H, F, Cl, amino, hydroxy, methoxy, or cyano.

5. The compound of claim 4, wherein the compound is of Formula Ia; X is Br; $R^4$ is H, methoxy, or cyano; $R^2$ is H, amino, or hydroxy; and $R^3$, $R^5$, and $R^6$ are each H.

6. The compound of claim 4, wherein the compound is of Formula Ib; X is F or Br; $R^6$ is H; $R^5$ is H, F, or Cl; $R^3$ and $R^4$ are each H, Cl, or hydroxy; and $R^2$ is H or hydroxy.

7. The compound of claim 1, wherein the compound is of Formula 1b, R' is pyrrol-2-yl, and X is F or Br.

8. A pharmaceutical composition comprising a pharmaceutically acceptable carrier and a compound, or a pharmaceutically acceptable salt thereof, of either Formula Ia or Formula Ib:

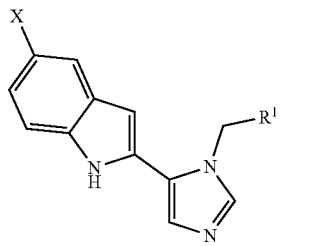
(Ia)

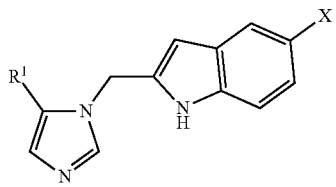
(Ib)

wherein

X is H, F, Cl, or Br;

$R^1$ is piperidin-2-yl, 1-phenylmethan-1-yl-1-ol, pyrrol-2-yl, or

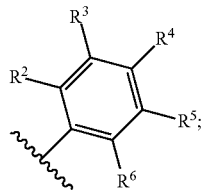

and $R^2$, $R^3$, $R^4$, $R^5$, and $R^6$ are each independently H, F, Cl, amino, hydroxy, alkoxy, cyano, trifluoromethyl, or phenyl.

* * * * *